United States Patent
Groh

(10) Patent No.: US 9,918,853 B2
(45) Date of Patent: Mar. 20, 2018

(54) SYSTEM FOR TREATING PROXIMAL HUMERAL FRACTURES AND METHOD OF USING THE SAME

(71) Applicant: ENCORE MEDICAL LP, Austin, TX (US)

(72) Inventor: Gordon I Groh, Asheville, NC (US)

(73) Assignee: ENCORE MEDICAL LP, Austin, TX (US)

( * ) Notice: Subject to any disclaimer, the term of this patent is extended or adjusted under 35 U.S.C. 154(b) by 137 days.

(21) Appl. No.: 14/970,447

(22) Filed: Dec. 15, 2015

(65) Prior Publication Data

US 2016/0095722 A1    Apr. 7, 2016

Related U.S. Application Data

(60) Division of application No. 13/910,694, filed on Jun. 5, 2013, now Pat. No. 9,241,723, which is a (Continued)

(51) Int. Cl.
*A61B 17/17* (2006.01)
*A61F 2/46* (2006.01)
(Continued)

(52) U.S. Cl.
CPC ........ *A61F 2/4612* (2013.01); *A61B 17/1725* (2013.01); *A61B 17/1778* (2016.11);
(Continued)

(58) Field of Classification Search
CPC ............ A61B 17/1664; A61B 17/1684; A61B 17/1725; A61B 17/164; A61F 2002/4074
See application file for complete search history.

(56) References Cited

U.S. PATENT DOCUMENTS

| 5,725,592 A | 3/1998 | White et al. |
| 5,961,555 A | 10/1999 | Huebner |

(Continued)

FOREIGN PATENT DOCUMENTS

| EP | 1952788 A1 | 8/2008 |
| EP | 2002794 A1 | 12/2008 |

OTHER PUBLICATIONS

International Search Report and Written Opinion for International Application No. PCT/US2010/024433 dated Sep. 29, 2010.

(Continued)

*Primary Examiner* — Samuel Hanna
(74) *Attorney, Agent, or Firm* — EIP US LLP

(57) ABSTRACT

Various embodiments of the present invention provide systems and methods for treating a proximal humeral fracture. A system according to one embodiment includes a longitudinal member configured to be received within the humeral shaft. The system includes a jig assembly configured to be coupled to the longitudinal member, wherein the jig assembly includes at least one hole defined therethrough that is configured to guide placement of at least one hole in the humeral shaft, and wherein the hole formed in the humeral shaft is configured to align with at least one hole in the humeral implant such that the jig assembly is configured to locate the position of the humeral implant in the humeral shaft.

4 Claims, 32 Drawing Sheets

Related U.S. Application Data continuation of application No. 12/707,238, filed on Feb. 17, 2010, now Pat. No. 8,480,677.

(60) Provisional application No. 61/154,064, filed on Feb. 20, 2009.

(51) Int. Cl.
*A61B 17/72* (2006.01)
*A61F 2/40* (2006.01)
*A61F 2/30* (2006.01)

(52) U.S. Cl.
CPC ............... *A61B 17/72* (2013.01); *A61F 2/40* (2013.01); *A61F 2/4014* (2013.01); *A61F 2/4684* (2013.01); *A61F 2002/30616* (2013.01); *A61F 2002/30617* (2013.01); *A61F 2002/30772* (2013.01); *A61F 2002/30785* (2013.01); *A61F 2002/4018* (2013.01); *A61F 2002/4029* (2013.01); *A61F 2002/4628* (2013.01); *A61F 2002/4687* (2013.01); *A61F 2250/0097* (2013.01)

(56) References Cited

U.S. PATENT DOCUMENTS

| | | |
|---|---|---|
| 6,168,627 B1 | 1/2001 | Huebner |
| 6,168,628 B1 | 1/2001 | Huebner |
| 6,277,123 B1 | 8/2001 | Maroney et al. |
| 6,283,999 B1 | 9/2001 | Rockwood, Jr. |
| 6,494,913 B1 | 12/2002 | Huebner |
| 6,558,425 B2 | 5/2003 | Rockwood, Jr. |
| 6,702,824 B2 | 3/2004 | Maroney et al. |
| 8,480,677 B2 | 7/2013 | Groh |
| 2001/0037115 A1 | 11/2001 | Maroney et al. |
| 2002/0151897 A1 | 10/2002 | Zirkle, Jr. |
| 2003/0135211 A1 | 7/2003 | Cho |
| 2003/0149486 A1 | 8/2003 | Huebner |
| 2007/0244563 A1 | 10/2007 | Roche et al. |
| 2009/0270867 A1 | 10/2009 | Poncet |
| 2011/0190769 A1* | 8/2011 | Haininger ............ A61B 17/72 606/64 |

OTHER PUBLICATIONS

Delta-Xtend™ Reverse Shoulder System, DePuy Orthopaedics, Inc., a Johnson-Johnson Company, 2007, 64 pages.

Global™ Fx Shoulder Fracture System, DePuy Orthopaedics, Inc., a Johnson-Johnson Company, 1999, 33 pages.

Global™ Fx Shoulder Fracture System, Positioning Jig, DePuy Orthopaedics, Inc., a Johnson-Johnson Company, 2003, 4 pages.

Shoulder Surgery Options, DePuy Orthopaedics, Inc., a Johnson-Johnson Company, 2005, 8 pages.

Delta-CTA Reverse Shoulder System, Surgical Technique Rehabilitating Function, DePuy Orthopaedics, Inc., a Johnson-Johnson Company, 2006, 32 pages.

Equinoxe® Stem Positioning Device—Exactech, Inc. [online][retrieved Jan. 30, 2009]. Retrieved from the Internet: . 1 page.

Equinoxe® Fracture Shoulder System—Exactech, Inc. [online][retrieved Jan. 30, 2009]. Retrieved from the Internet: . 1 page.

Exactech Shoulder Prostheses [online][retrieved Feb. 3, 2009]. Retrieved from the Internet: . 1 page.

Acumed® For the Treatment of Proximal Humeral Fractures, Polarus Modular Shoulder, 2 pages, 2005.

\* cited by examiner

SYSTEM FOR TREATING PROXIMAL HUMERAL FRACTURES AND METHOD OF USING THE SAME

CROSS-REFERENCE TO RELATED APPLICATIONS

The present application is a divisional of U.S. application Ser. No. 13/910,694, filed Jun. 5, 2013, which is a continuation of U.S. application Ser. No. 12/707,238, filed Feb. 17, 2010, now U.S. Pat. No. 8,480,677, titled "System For Treating Proximal Humeral Fractures And Method Of Using The Same," which claims priority from U.S. Provisional Application No. 61/154,064, filed Feb. 20, 2009, the contents of which are incorporated herein by reference.

BACKGROUND OF THE INVENTION

Field of the Invention

Various embodiments of the present invention relate to systems and methods for treating proximal humeral fractures and, in particular, to a system for locating and positioning an implant within the humeral shaft for treating a proximal humeral fracture, wherein the system is capable of being used for standard and reverse shoulder arthroplasty and hemiarthroplasty.

Description of the Related Technology

Total shoulder replacement or arthroplasty may be indicated for those with severe arthritis, a fractured proximal humeral, or other complications. There are different types of arthroplasty procedures that may be performed depending on the patient. For example, total shoulder arthroplasty generally involves replacing the damaged bone and cartilage with an implant. For a conventional shoulder arthroplasty, a metal implant having a head is positioned within the humerus, and a polymeric socket is implanted within the scapula. A hemiarthroplasty involves replacing only one half of the shoulder joint, which may be suitable for patients with proximal humeral fractures. Another technique for replacing the shoulder is a reverse shoulder arthroplasty where the location of the head and socket are reversed, which may be indicated for patients that have completely torn rotator cuffs.

Proximal humeral fractures treated with arthroplasty continue to be challenging for the orthopedic surgeon. One of the difficulties is the amount of proximal humeral bone loss, which must be compensated for in selecting final component position. Previous systems have attempted to address these issues by incorporating a jig system to compensate for these anatomical deficiencies. For example, U.S. Pat. No. 6,277, 123 to Maroney et al. discloses one such jig system employing a clamp that attaches to the humeral shaft. However, there are difficulties that remain even with this jig in place both for hemiarthroplasty and reverse shoulder arthroplasty in the treatment of cases with proximal humeral bone loss. First, utilization of this jig requires a more extensive surgical dissection to seat the jig. Second, the jig is by nature quite bulky and unwieldy in the surgical wound. Third, the alignment apparatus is not configured for utilization in reverse arthroplasty. Fourth, the amount of force required to reduce a reverse arthroplasty is much greater than in a hemiarthroplasty application. This amount of force may cause the jig to fail at either the implant interface or bone interface.

Thus, there remains a need in the art for an improved system for treating proximal humeral fractures. In particular, there is a need for less complex and bulky system. In addition, there is a need for a system that is applicable to both hemiarthroplasty and reverse arthroplasty that builds off the existing shoulder platform.

SUMMARY

The above and other needs may be met by embodiments of the present invention which, in one embodiment, provides a system for treating a proximal humeral fracture. According to one embodiment, a system for treating a proximal humeral fracture with a humeral implant having at least one hole defined therethrough is provided. The system includes a longitudinal member configured to be at least partially received within the humeral shaft and a jig assembly configured to be coupled to the longitudinal member. The jig assembly includes at least one hole defined therethrough that is configured to guide placement of at least one hole in the humeral shaft, wherein the at least one hole formed in the humeral shaft is configured to align with the at least one hole in the humeral implant such that the jig assembly is configured to locate the position of the humeral implant in the humeral shaft.

According to one aspect, the system includes a longitudinal member including at least one hole defined therethrough, wherein at least a portion of the longitudinal member including the at least one hole is configured to be received within the humeral shaft. In another aspect, the system includes a jig assembly configured to be coupled to the longitudinal member, wherein the jig assembly includes at least one hole defined therethrough that is configured to align with the hole of the longitudinal member and guide placement of at least one hole in the humeral shaft, and wherein the at least one hole formed in the humeral shaft is configured to align with at least one hole in the humeral implant such that the longitudinal member and the jig assembly are configured to locate the position of the humeral implant in the humeral shaft. According to various aspects of the system, the longitudinal member and the jig assembly each includes a plurality of holes that are configured to align with one another. The at least one hole in the longitudinal member and the at least one hole in the jig assembly may be configured to receive a drill bit therethrough and guide placement of a bicortical or unicortical hole in the humeral shaft. The holes in the longitudinal member and jig assembly may also be configured to guide placement of a bicortical or unicortical pin in the humeral shaft. In addition, the longitudinal member may include a plurality of holes defined therethrough at different radial and axial locations that are configured to determine a retroversion of the humeral implant.

The system may also include a fin clamp assembly including at least one hole defined therethrough that is configured to align with the at least one hole in the humeral implant and the hole in the humeral shaft, wherein the fin clamp assembly includes a fin clamp configured to be coupled to a fin of the humeral implant. The fin clamp may include an extension member and a pin guide coupled thereto, wherein the pin guide comprises the at least one hole configured to align with the at least one hole in the humeral implant and the hole in the humeral shaft, and wherein the extension member is slidably engaged with the fin clamp for adjusting a relative distance between the pin guide and the fin clamp. Furthermore, the longitudinal member may include a coupling member configured to abut the proximal end of the humeral shaft, wherein the jig assembly includes a coupling member configured to mate with the coupling member of the longitudinal member. In another aspect, the jig assembly further comprises a guide slidably engaged with an arm extending from the coupling member thereof for adjusting a relative distance between the guide and the arm. The jig assembly may also include a pin guide comprising the at least one hole, wherein the pin guide is slidably engaged with the guide for adjusting a relative axial position of the pin guide with respect to the guide.

An additional embodiment of the present invention is directed to a method for treating a proximal humeral fracture with a humeral implant having at least one hole defined therethrough. The method includes inserting at least a portion of a longitudinal member within the humeral shaft and coupling a jig assembly including at least one hole defined therethrough to the longitudinal member. The method further includes forming at least one hole in the humeral shaft guided by the hole of the jig assembly, wherein the at least one hole formed in the humeral shaft is configured to align with the at least one hole in the humeral implant such that the jig assembly is configured to locate the position of the humeral implant in the humeral shaft.

In one aspect, the method includes inserting at least a portion of a longitudinal member including at least one hole defined therethrough within the humeral shaft and coupling a jig assembly including at least one hole defined therethrough to the longitudinal member such that the least one hole defined in the jig assembly aligns with the at least one hole of the longitudinal member. In another aspect, the method further includes forming at least one hole in the humeral shaft guided by the aligned holes of the jig assembly and longitudinal member, wherein the at least one hole formed in the humeral shaft is configured to align with the at least one hole in the humeral implant such that the longitudinal member and the jig assembly are configured to locate the position of the humeral implant in the humeral shaft.

Additional aspects of the method include removing the longitudinal member from the humeral shaft and inserting a trial humeral implant having at least one hole defined therethrough within the humeral shaft. The method may also include inserting a cortical (i.e., bicortical or unicortical) pin through the hole in the humeral shaft and the hole defined in the trial humeral implant. Furthermore, the method may include aligning a first hole defined in a fin clamp assembly with the cortical pin and coupling the fin clamp assembly to the trial humeral implant. The method may include inserting a unicortical pin in the humeral shaft that is configured to align with a second hole defined in the fin clamp assembly. The method may include removing the cortical pin from the trial humeral implant and removing the trial humeral implant from the humeral shaft. Moreover, the method may include inserting a final humeral implant having at least one hole defined therethrough within the humeral shaft. The method may also include aligning the first and second holes of the fin clamp assembly with the respective cortical and unicortical pins and coupling the fin clamp assembly to the final humeral implant.

According to another embodiment, a humeral implant for treating a proximal humeral fracture is provided. The humeral implant includes a proximal end and a distal end and a longitudinal axis extending therebetween, wherein at least the distal end is configured for insertion within a humeral shaft. The humeral implant also includes a plurality of holes defined therethrough and transversely to the longitudinal axis, wherein each of the holes is configured to align with a hole defined in the humeral shaft for locating the position of the humeral implant in the humeral shaft. In accordance with one aspect, the humeral implant is modular and includes a body and a stem that are interchangeably coupled to one another, wherein the plurality of holes are formed through the stem.

An additional embodiment is directed to a kit for treating a proximal humeral fracture. The kit includes a humeral implant comprising at least one hole defined therethrough, a longitudinal member configured to be at least partially received within the humeral shaft, and a jig assembly configured to be coupled to the longitudinal member. The jig assembly further includes at least one hole defined therethrough that is configured to guide placement of at least one hole in the humeral shaft, wherein the at least one hole formed in the humeral shaft is configured to align with the at least one hole in the humeral implant such that the jig assembly is configured to locate the position of the humeral implant in the humeral shaft.

Aspects of the kit are directed to a longitudinal member including at least one hole defined therethrough, wherein at least a portion of the longitudinal member comprising the at least one hole is configured to be received within the humeral shaft. The kit may also include a jig assembly having at least one hole defined therethrough that is configured to align with the at least one hole of the longitudinal member and guide placement of at least one hole in the humeral shaft. In addition, the hole formed in the humeral shaft is configured to align with the at least one hole in the humeral implant such that the longitudinal member and the jig assembly are configured to locate the position of the humeral implant in the humeral shaft. The kit may optionally include a fin clamp assembly that includes at least one hole defined therethrough that is configured to align with the at least one hole in the humeral implant and the at least one hole in the humeral shaft, wherein the fin clamp assembly is further configured to be coupled to the humeral implant. Moreover, the kit may include at least one trial humeral implant and at least one final humeral implant.

An additional system embodiment includes a jig assembly comprising at least one hole defined therethrough that is configured to guide placement of at least one bicortical or unicortical hole in the humeral shaft. The hole formed in the humeral shaft is configured to align with the at least one hole in the humeral implant such that the jig assembly is configured to locate the position of the humeral implant in the humeral shaft prior to implanting the humeral implant in the humeral shaft.

Moreover, a further system embodiment includes a fin clamp assembly comprising at least one hole defined therethrough that is configured to align with the at least one hole in the humeral implant and at least one hole previously formed in the humeral shaft. The fin clamp assembly is further configured to be coupled to the humeral implant to locate and secure the humeral implant in the humeral shaft.

A further embodiment is directed to a system for treating a proximal humeral fracture with a humeral implant having at least one hole defined therethrough. The system includes a broach assembly configured to be coupled to the humeral implant and a jig assembly configured to be coupled to the broach assembly. The jig assembly includes at least one hole defined therethrough that is configured to align with the at least one hole of the humeral implant and guide placement of at least one hole in the humeral shaft for locating the position of the humeral implant in the humeral shaft.

BRIEF DESCRIPTION OF THE DRAWINGS

Various embodiments of the invention will be better understood by reference to the Detailed Description of Various Embodiments of the Invention when taken together with the attached drawings, wherein.

DETAILED DESCRIPTION OF CERTAIN INVENTIVE EMBODIMENTS

Figure 1:
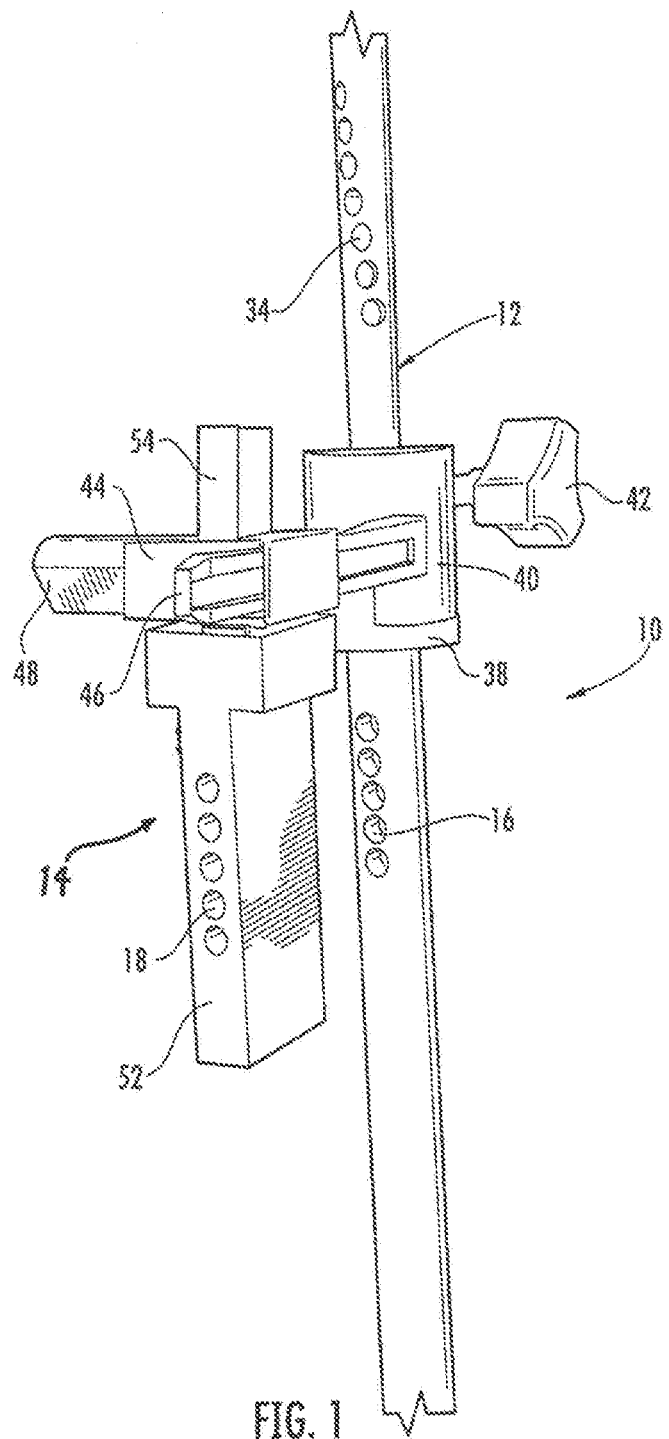
FIG. 1 is a perspective view of a system for treating a proximal humeral fracture including a longitudinal member and a jig assembly according to one embodiment of the present invention.

Various embodiments of the present invention now will be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like numbers refer to like elements throughout. The singular forms "a," "an," and "the" include plural referents unless the context clearly dictates otherwise.

As shown generally in FIGS. 1 and 4-9, embodiments of the present invention generally provide a system 10 that includes a longitudinal member 12 and a jig assembly 14. Both the longitudinal member 12 and jig assembly 14 include respective holes 16, 18 that are configured to align with one another in order to locate the position of a humeral implant 22 in the humeral shaft 26. As shown in FIGS. 24-28, the system 10 also includes a fin clamp assembly 20 that is configured to be coupled to a humeral implant 22. The fin clamp assembly 20 includes one or more holes 24 that are also configured to locate and position the humeral implant 22 within the humeral shaft 26. As explained in further detail below, the system 10 is capable of locating and positioning the humeral implant within the humeral shaft even where there is substantial proximal humeral bone loss.

The system 10 is generally configured for positioning and placement of a humeral implant 22 within a humeral shaft 26. In particular, the system 10 may be used for standard and reverse shoulder arthroplasty or hemiarthroplasty procedures. The system 10 is also indicated for proximal humeral fractures where there is proximal humeral bone loss, such as where all or a portion of the humeral head has been fractured. Although the embodiments are discussed in conjunction for treatment of proximal humeral fractures, it is understood that the system may be adapted for other long bones in accordance with additional embodiments of the present invention. For example, the system 10 may be modified for use with long bones such as the tibia or femur where an end of the bone has been fractured.

Figure 2:
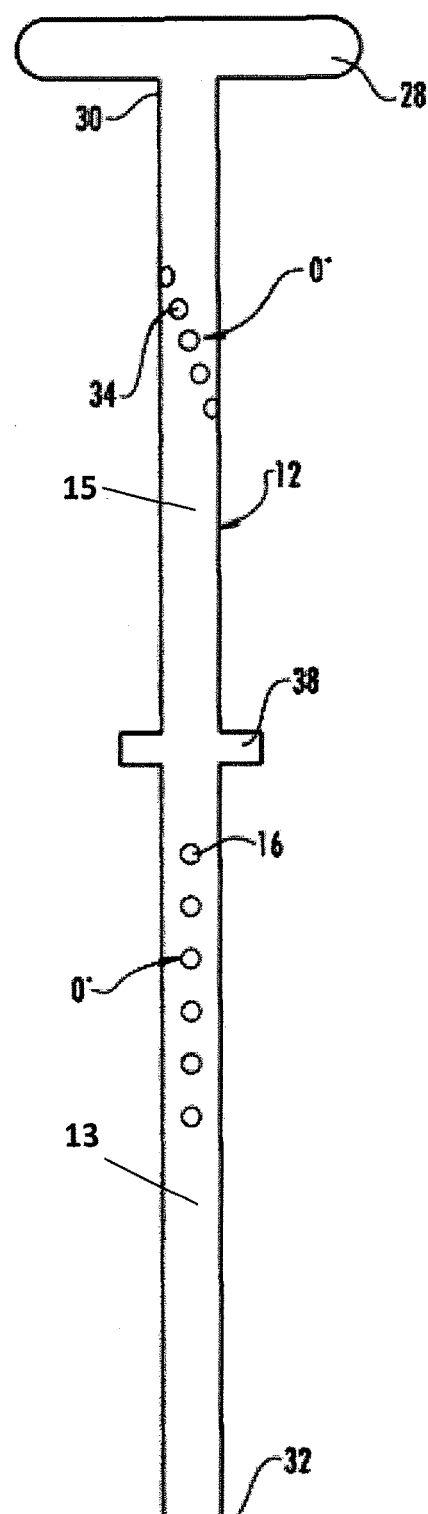
FIG. 2 is a side view of a longitudinal member according to one embodiment of the present invention.
Figure 3:
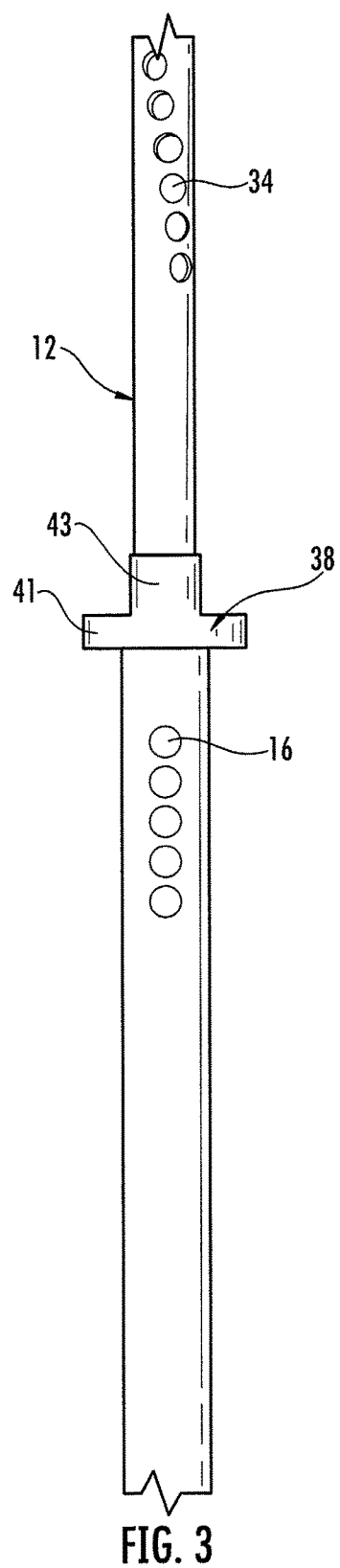
FIG. 3 is an enlarged side view of the longitudinal member shown in FIG. 2.

Referring to FIGS. 2 and 3, there is shown a longitudinal member 12 according to one embodiment of the present invention. The longitudinal member 12 has a T-handle 28 at its proximal end 30 that is capable of being gripped by a physician for handling and positioning the longitudinal member in the humeral shaft 26. The distal end 32 of the longitudinal member 12 is configured for placement within the medullary canal of the humeral shaft 26. The longitudinal member 12 also includes a plurality of holes 34 that are offset radially and axially along the longitudinal member from one another. The holes 34 are configured to receive an orientation pin 36 that is used to determine the version of the humeral implant (see FIG. 6). For example, the version may be determined by positioning an orientation pin 36 through one of the holes 34 and comparing the orientation of the pin to the orientation of the patients forearm. The longitudinal member 12 may be rotated internally or externally to achieve a desired version. There may be any number of holes 34 that are offset at various angles from one another, such as 10° from one another within a range of about 0 to 40° of version.

Figure 4:
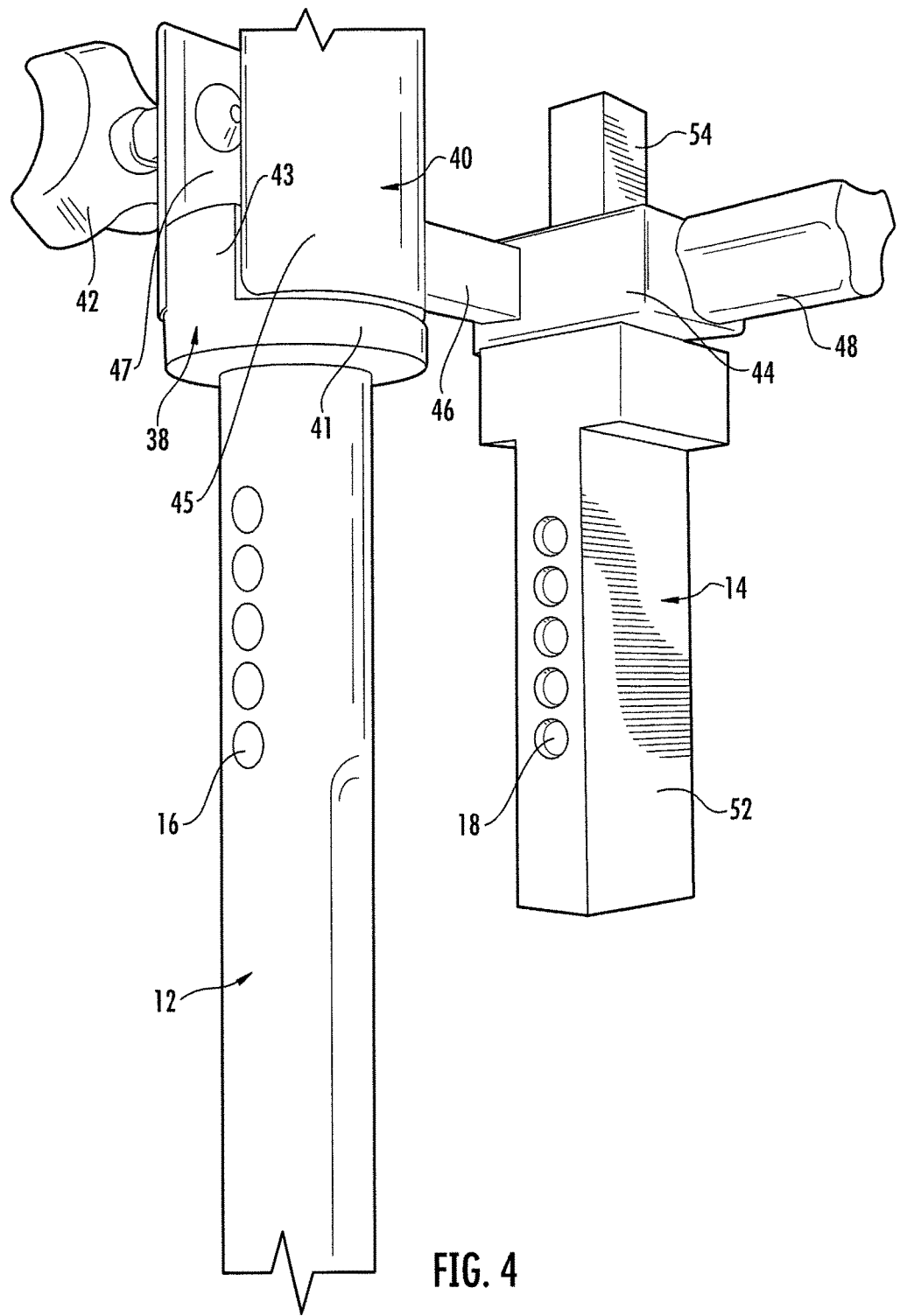
FIG. 4 is an enlarged perspective view of the jig assembly shown in FIG. 1.
Figure 5:
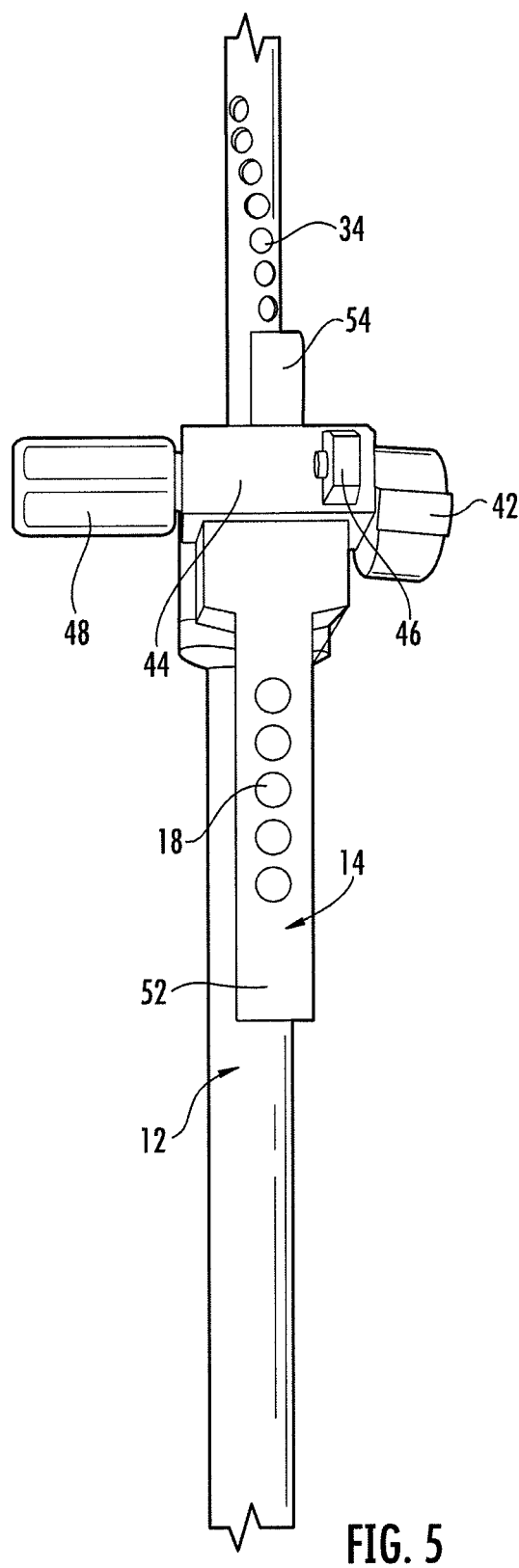
FIG. 5 is an enlarged side view of the jig assembly shown in FIG. 1.
Figure 6:
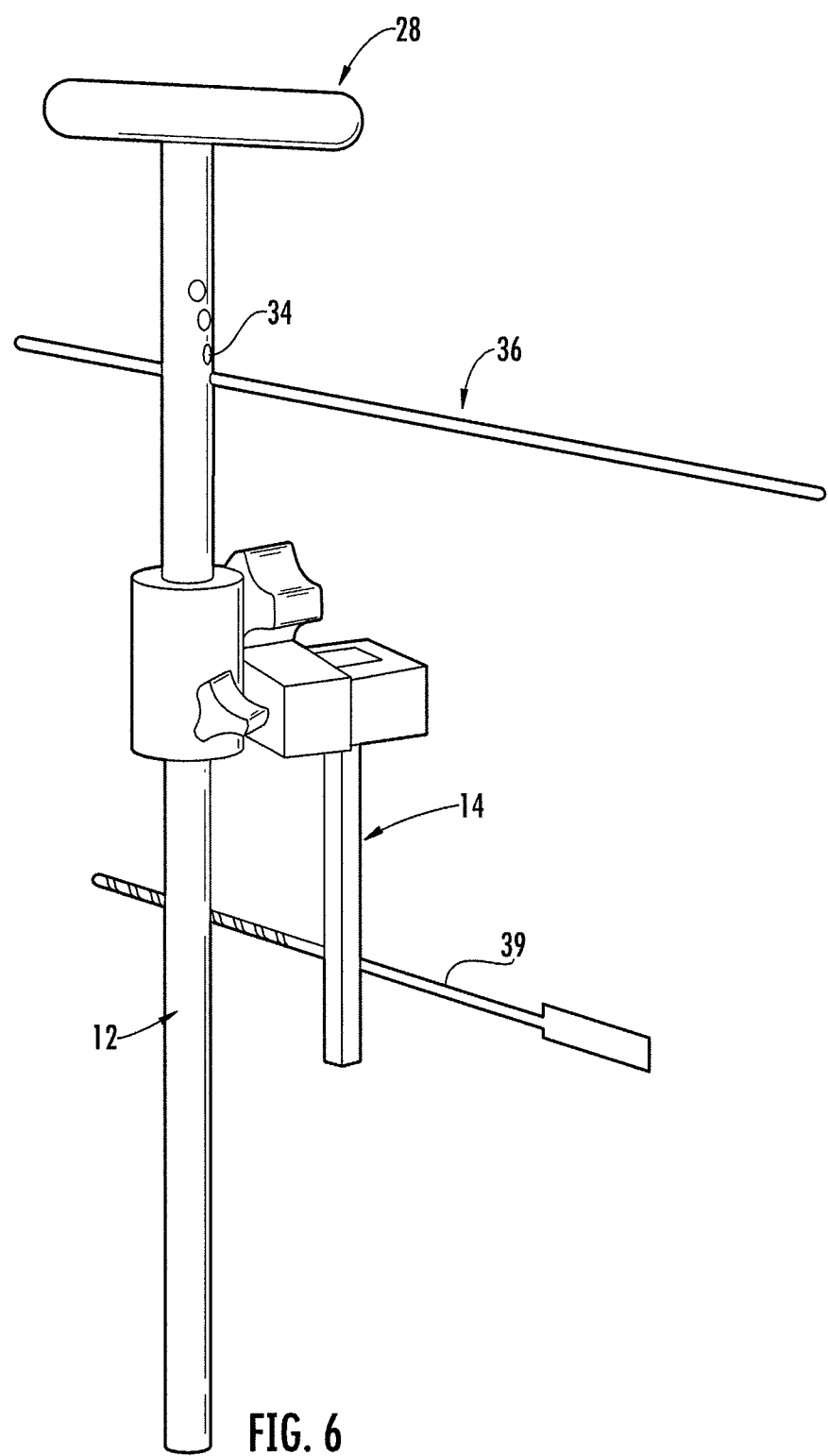
FIG. 6 is a perspective view of the jig system shown in FIG. 1 including an orientation pin and a drill bit positioned therethrough.
Figure 7:
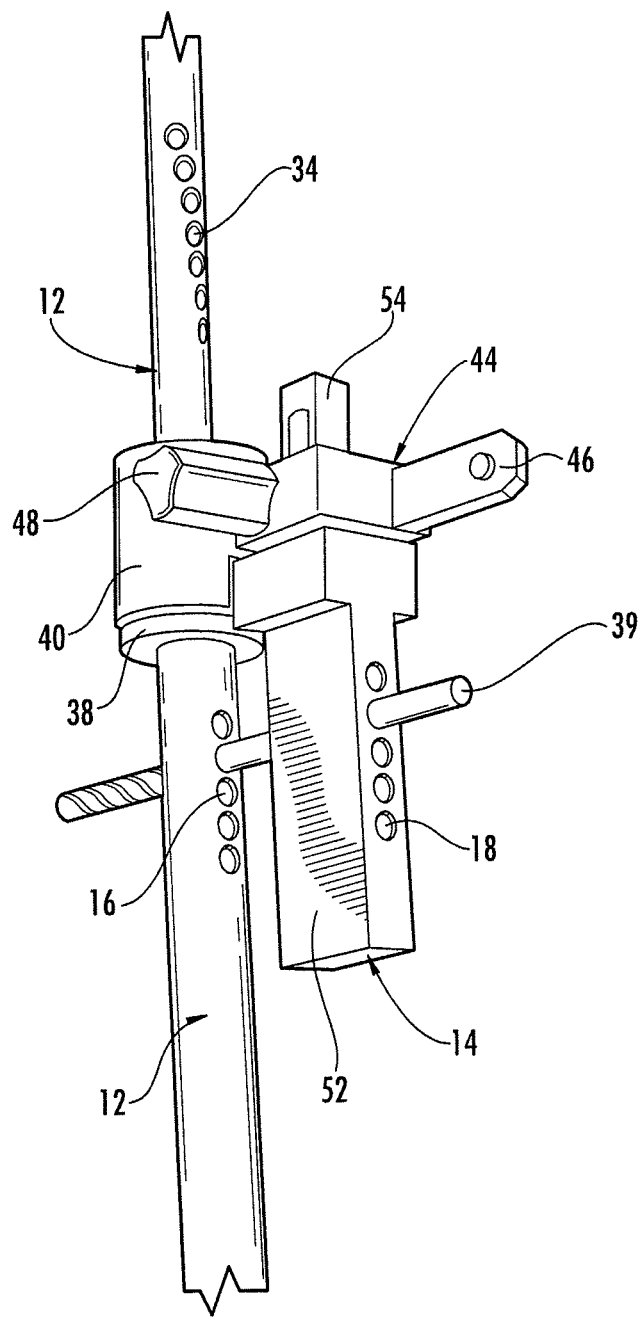
FIG. 7 is a perspective view of the jig assembly shown in FIG. 1 including a drill bit positioned therethrough.
Figure 8:
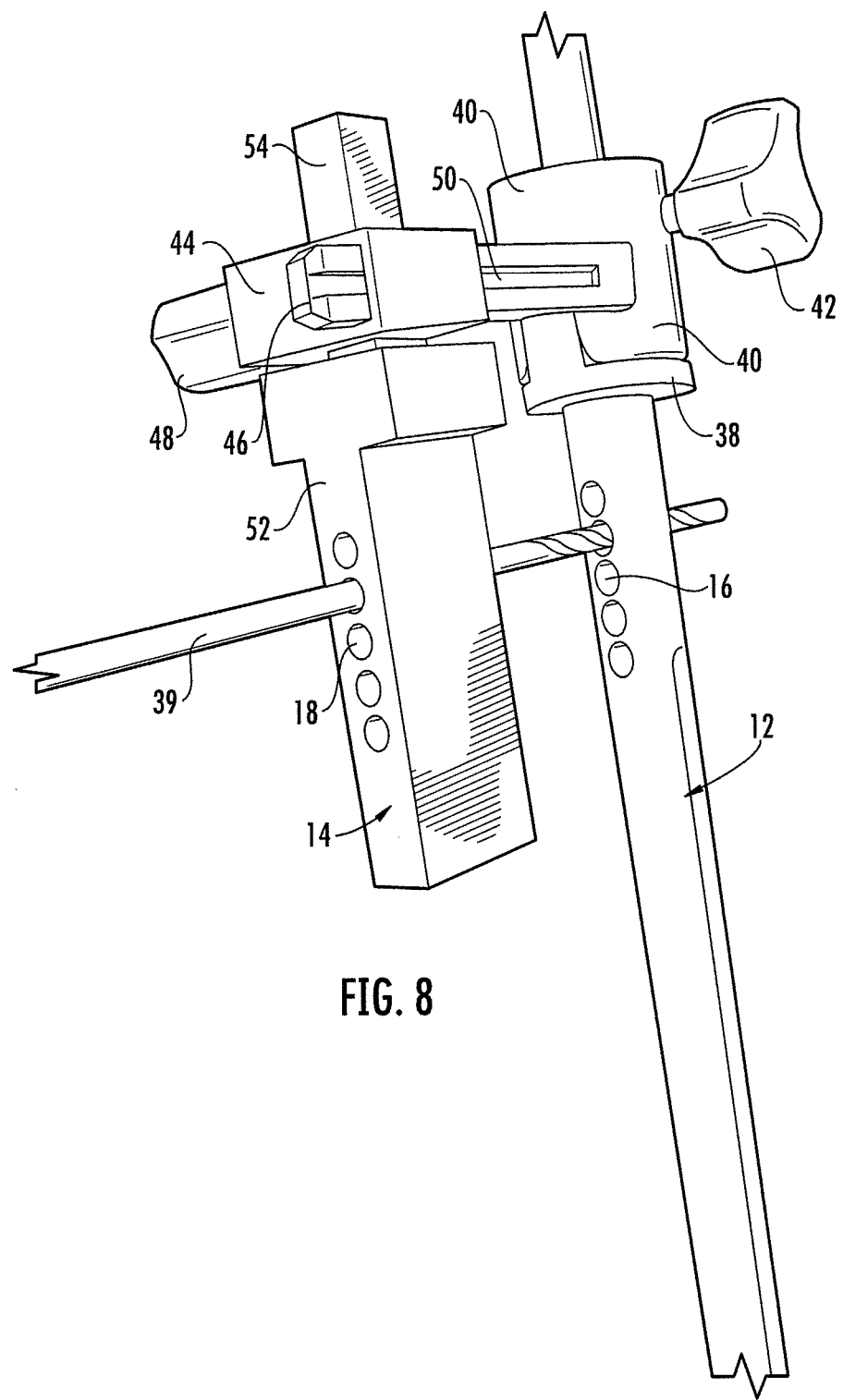
FIG. 8 is an enlarged perspective view of the jig assembly shown in FIG. 1 including a drill bit positioned therethrough.
Figure 9:
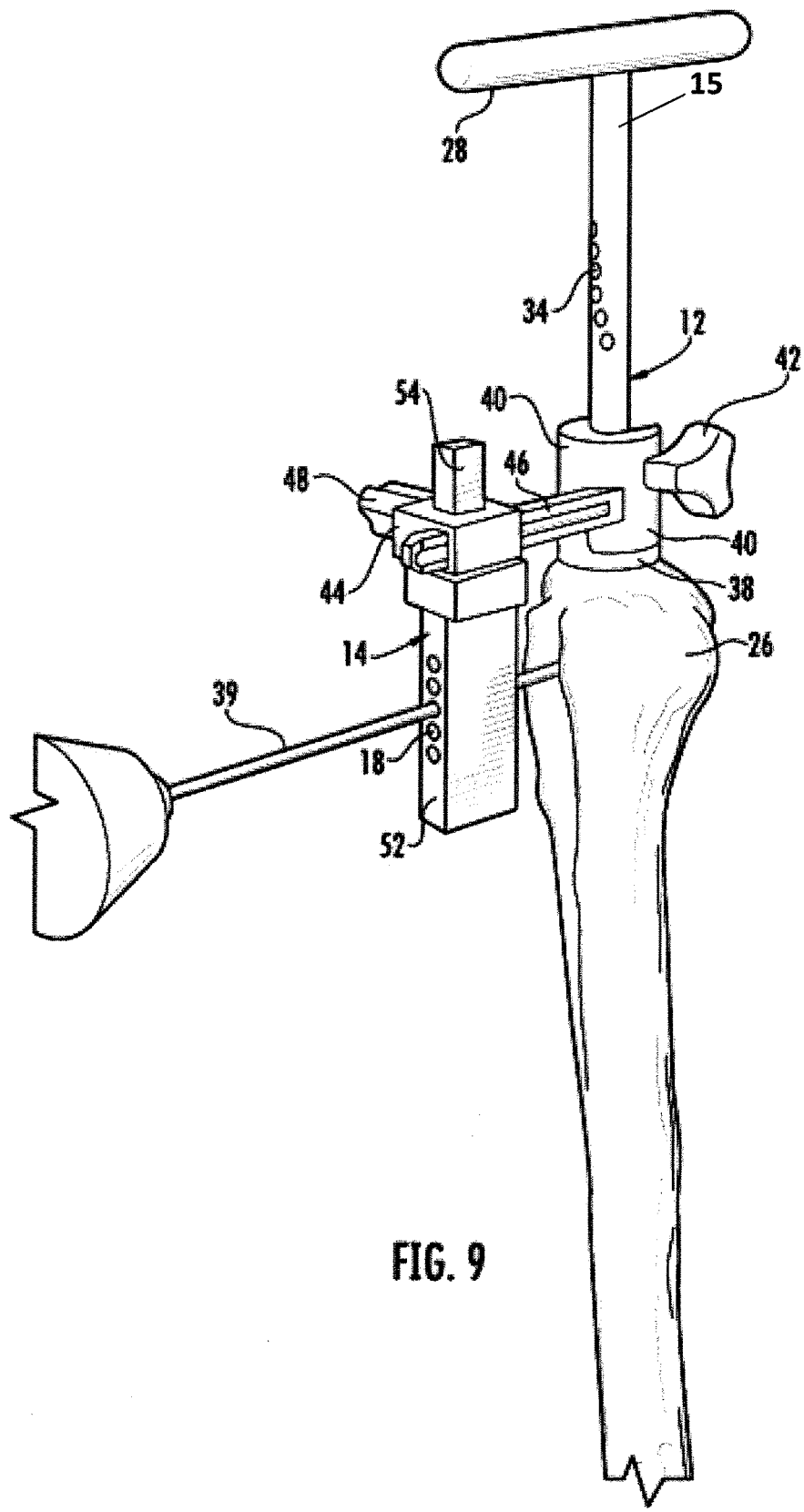
FIG. 9 is a perspective view of the system shown in FIG. 1 secured to the humeral shaft and including a drill bit positioned therethrough.
Figure 10:
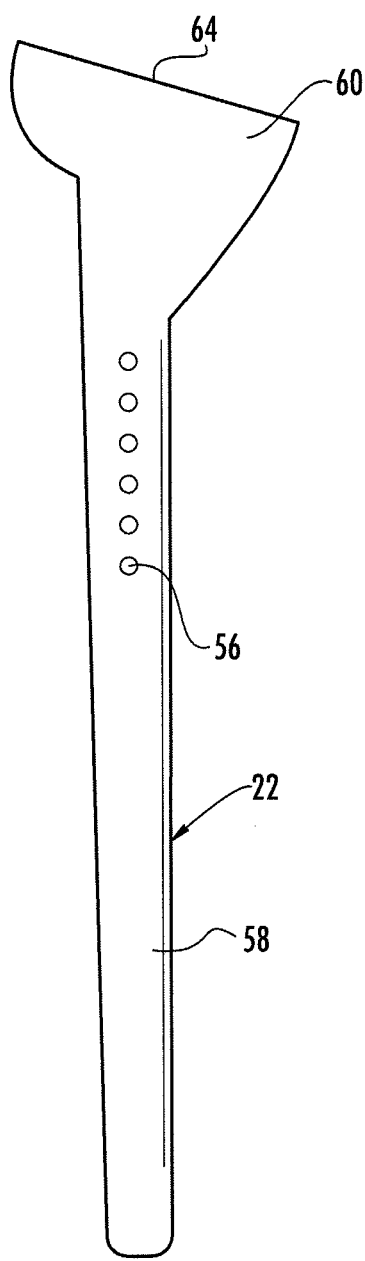
FIGS. 10 and 11 are side views of trial humeral implants compatible with the system shown in FIG. 1 according to embodiments of the present invention.
Figure 11:
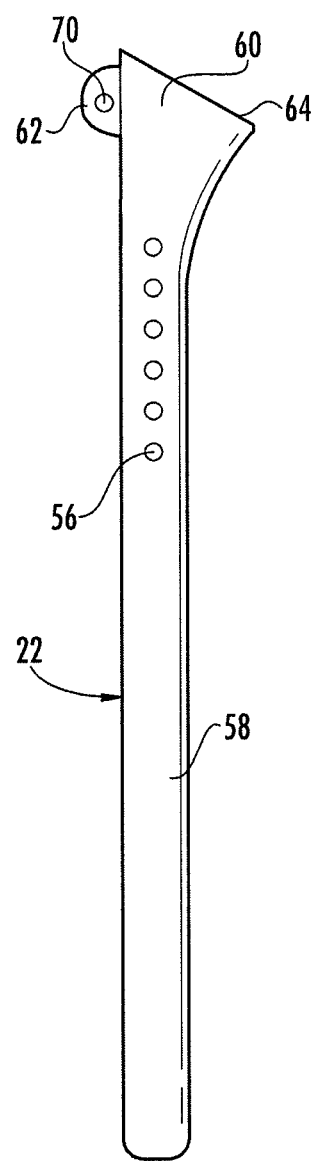
Figure 12:
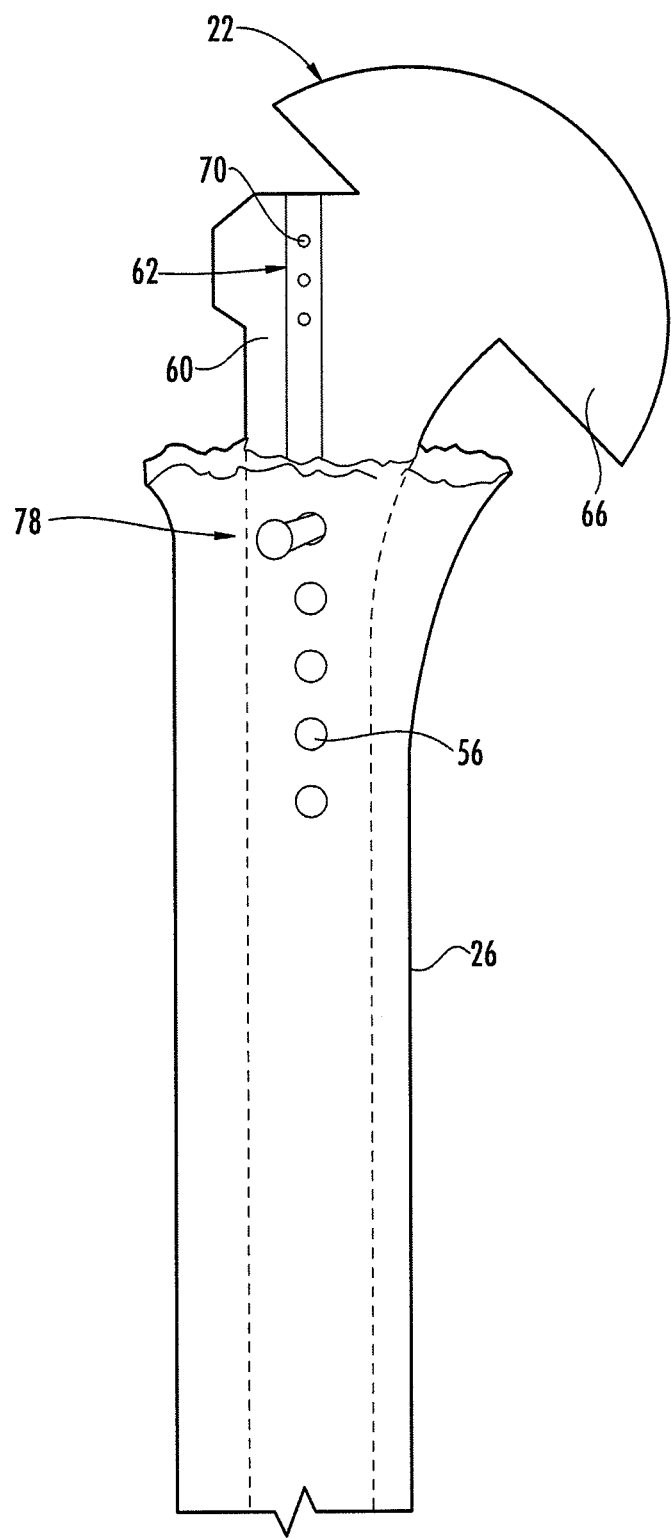
FIG. 12 is a side view of a final humeral implant positioned within the humeral shaft and secured thereto with a pin according to one embodiment of the present invention.
Figure 13:
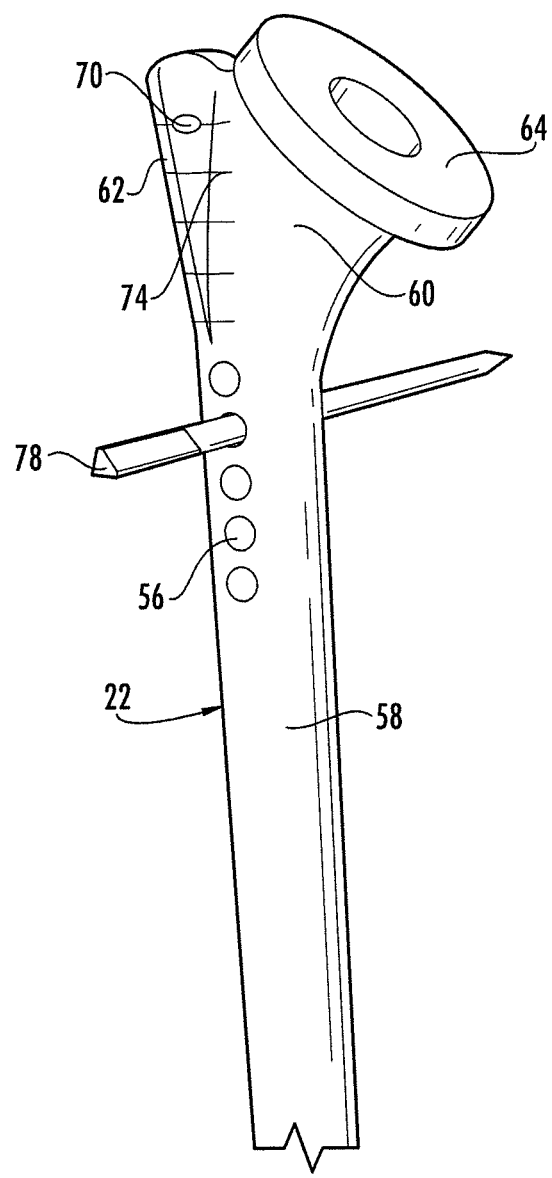
FIG. 13 is a perspective view of a humeral final implant having a pin positioned therethrough according to an embodiment of the present invention.
Figure 14:
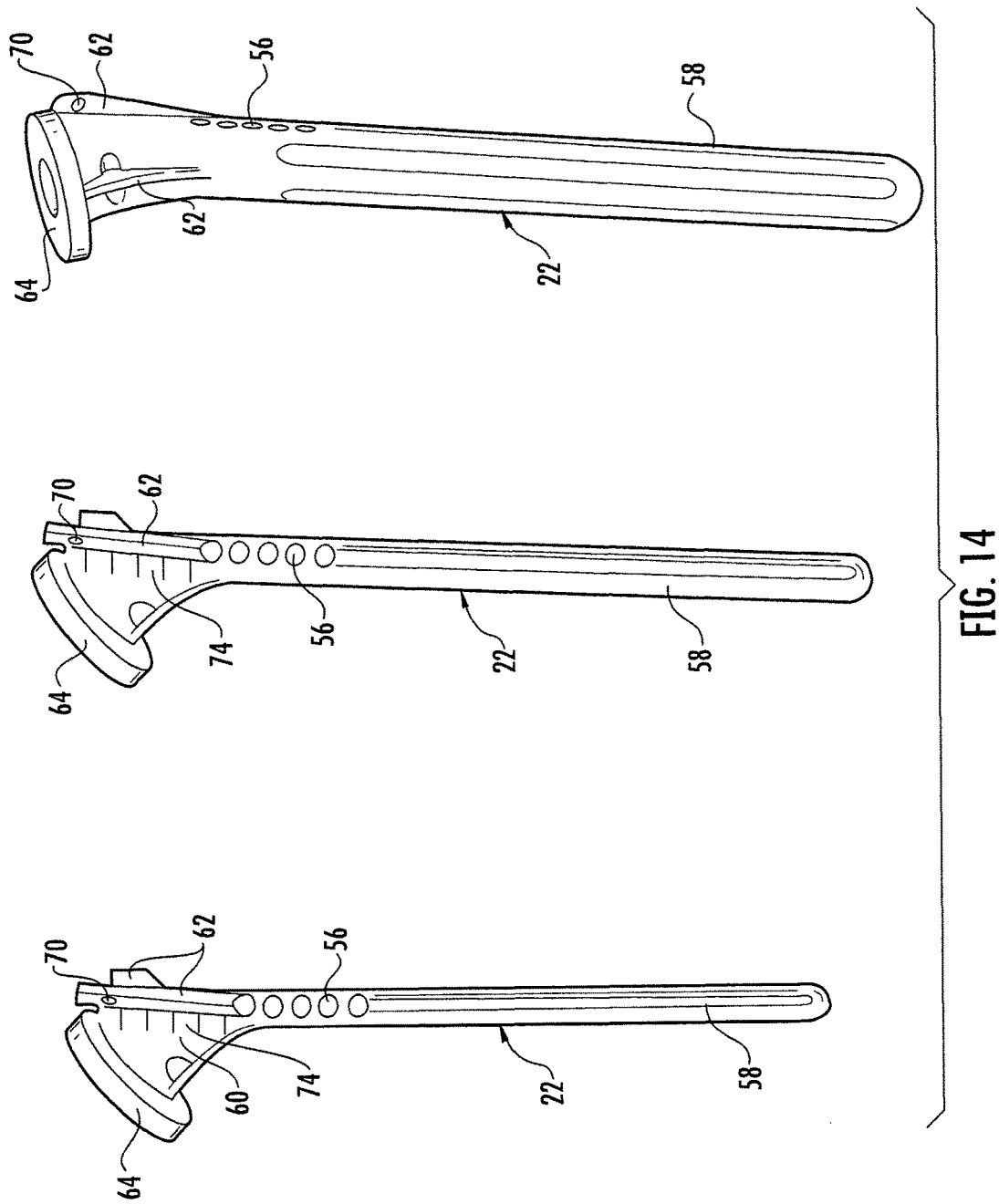
FIG. 14 illustrates different side views of final humeral implants having various sizes according to additional embodiments of the present invention.

In addition, the longitudinal member 12 includes a coupling member 38 that is configured to mate with a coupling member 40 of the jig assembly 14, wherein the coupling members may be secured together with a fastener 42, as shown in FIG. 4. In particular, the coupling member 38 includes a shoulder 41 and a raised portion 43, while the coupling member 40 includes a pair of clamp members 45 separated by a channel 47. The clamp members 45 are capable of being positioned around the longitudinal member 12 by positioning the longitudinal member within the channel. The clamp members 45 may abut the shoulder 43 and be secured to the longitudinal member 12 and the raised portion 43 with the fastener 42.

Figure 1A:
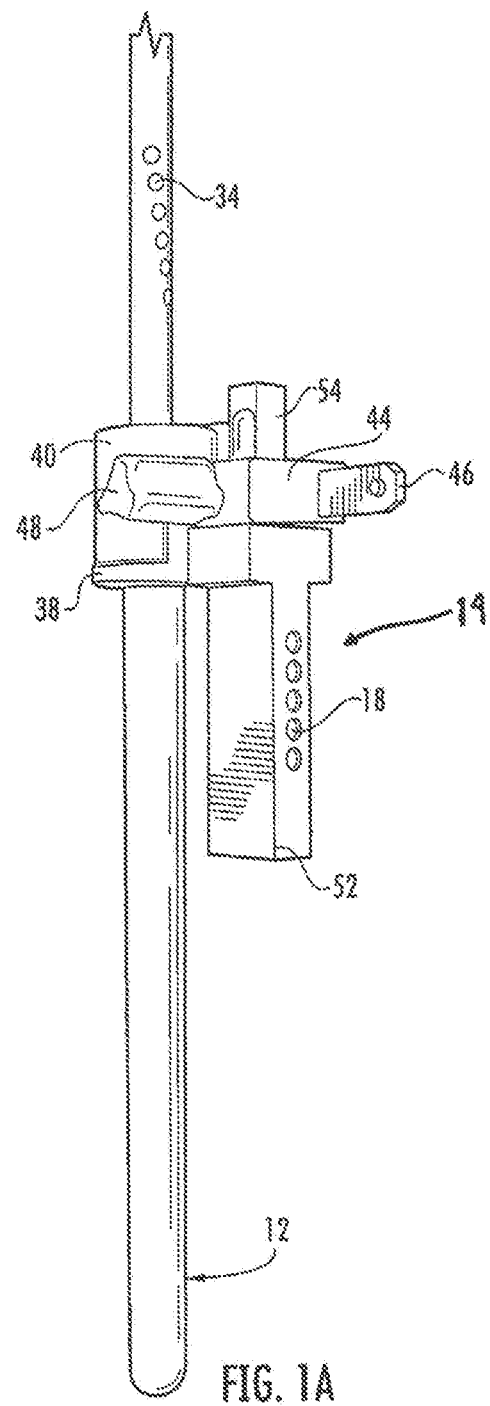
FIG. 1A is a perspective view of a system for treating a proximal humeral fracture including a longitudinal member and a jig assembly according to one embodiment of the present invention.

The longitudinal member 12 also includes a plurality of holes 16 located distally of the coupling member 38 that are configured to be disposed within the humeral shaft. The holes 16 are spaced axially apart from one another, such as about 3-5 mm from one another. The holes 16 are sized and configured to guide the formation of a cortical hole within the humeral shaft, such as by receiving and guiding a drill bit 39 therethrough (see FIGS. 6-8). Although five or six holes 16 are shown in FIGS. 1 and 2, there may be one or more holes depending on the amount of height adjustment desired in order to position the humeral implant 22 within the humeral shaft 26. Alternatively, FIG. 1A illustrates that the longitudinal member 12 may not have holes 16 defined therein, which may be used for placement of one or more unicortical holes in the humeral shaft 26 as described below.

The jig assembly 14 generally includes guide 44 coupled to an arm 46 extending from the coupling member 40. The arm 46 includes a groove 50 that is configured to mate with a corresponding ridge (not shown) within the guide 44. Thus, the guide 44 may slide along the arm 46 to adjust the distance between the guide and the coupling member 40. The jig assembly 14 also includes a pin guide 52 and an extension member 54. The extension member 54 is configured to be received within an opening (not shown) defined in the guide 44 such that the extension member is configured to move axially through the opening. Thus, the extension member 54 may be used to adjust the position of the pin guide 52 with respect to the guide 44. The guide 44 and extension member 54 may be secured together with a fastener 48 such that the position of the pin guide 52 may be fixed when the fastener is tightened. Although the position of the jig assembly 14 is disclosed as being adjustable, it is understood that the position of the guide 44 and/or pin guide 52 may be adjusted or even fixed in position such as by welding.

As stated above, the jig assembly 14 includes a plurality of holes 18 for facilitating the positioning of the humeral implant 22 in the humeral shaft 26. In particular, the pin guide 52 includes a plurality of holes 18 defined therethrough that are configured to align with the plurality of holes 16 defined in the longitudinal member 12. Thus, the holes 18 are also configured to guide the formation of a hole within the humeral shaft, such as by receiving and guiding a drill bit 39 therethrough (see FIGS. 6-8). The drill bit 39 is configured to be inserted within a hole 18 in the jig assembly 14 and a corresponding hole 16 in the longitudinal member 12, which may be useful for guiding a unicortical or bicortical hole into the humeral shaft 26. In the alternative, the longitudinal member 12 may not have holes 16 as shown in FIG. 1A such that the drill bit 39 is guided only by one of the holes 18 in the jig assembly 14, which may be used to guide a unicortical hole into the humeral shaft 26. As before, although five holes 18 are shown in FIG. 1, there may be one or more holes depending on the amount of height adjustment desired in order to position the humeral implant within the humeral shaft.

Moreover, the jig assembly 14 is able to transfer the version determined using the longitudinal member 12 and orientation pin 34 to the humeral implant 22 when one or more holes are drilled in the humeral shaft 26 while being guided by one or more corresponding holes 18. In particular, once the desired version is obtained using the orientation pin 36, the hole formed in the humeral shaft 26 via the jig assembly may memorize the version and allow the physician to insert a pin 78 in the humeral implant 22 and humeral shaft at the same version.

As indicated above, the system 10 is capable of being used to position a humeral implant 22 within the humeral shaft. FIGS. 10-14 show various humeral implants 22 according to embodiments of the present invention. The humeral implant 22 may include conventional features, such as a stem 58, a body 60, anterior, posterior, and/or lateral fins 62, and height indicators 74 (e.g., laser lines formed on the body). The fins 62 may include one or more holes 70 for receiving a suture. The humeral implant 22 may also include a collar 64 that may be configured to be coupled with a head 66 for a conventional shoulder arthroplasty (see FIG. 27), or may be configured as a socket for a reverse arthroplasty (see FIG. 28). Moreover, the humeral implant 22 may include a plurality of holes 56 defined therethrough. The holes 56 are configured to align with the holes 16, 18 defined in the longitudinal member 12 and jig assembly 14, respectively. As explained in further detail below, each of the holes 56 is sized and configured to receive a pin 78 in order to position the humeral implant 22 within the humeral shaft (see FIGS. 12 and 13). The holes 56 may be defined in both a trial humeral implant that is used to determine the position of the final humeral implant, as well as the final humeral implant, which is also explained in further detail below. It is understood that the humeral implant 22 may be various sizes and configurations for accommodating patients having varying sizes and injuries. For instance, the stem 58 length may range between about 100 and 250 mm, the stem diameter may range between about 4 to 20 mm, and the head 66 may have a radius of about 40 to 60 mm and a height of about 10 to 30 mm. The humeral implant 22 is typically a metal material (e.g., titanium or cobalt chromium), and the body 60 may optionally include a porous coating for facilitating fixation with bone. According to one embodiment, the humeral implant 22 may be similar to that disclosed by U.S. Pat. No. 6,283,999 to Rockwood, Jr., which is incorporated herein by reference, wherein the humeral implant may be modified for use with the system 10 by forming holes 56 in the stem 58.

Figure 19:
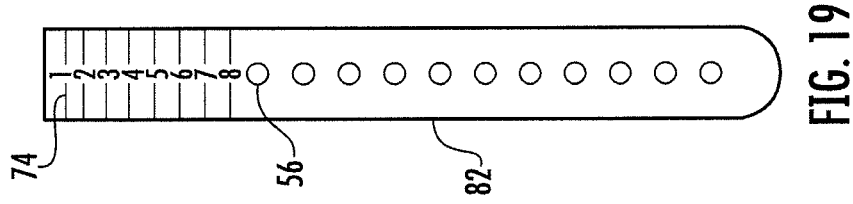
FIGS. 18 and 19 are side views of a modular trial humeral implant according to an additional embodiment of the present invention.
Figure 18:
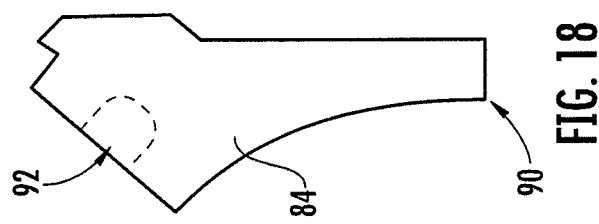
Figure 17:
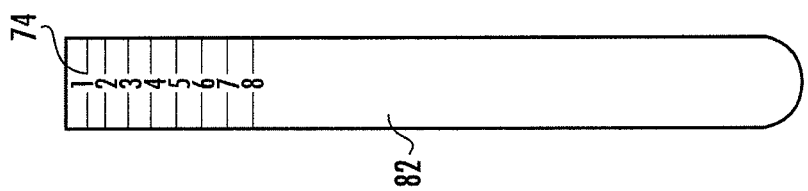
FIGS. 15-17 are side views of a modular final humeral implant according to an additional embodiment of the present invention.
Figure 16:
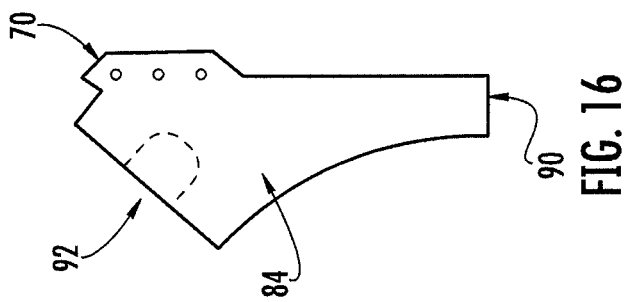
Figure 17A:
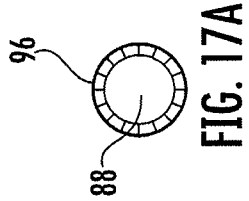
FIG. 17A is an end view of the stem shown in FIG. 17.
Figure 15:
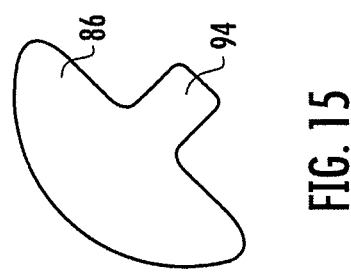
Figure 20:
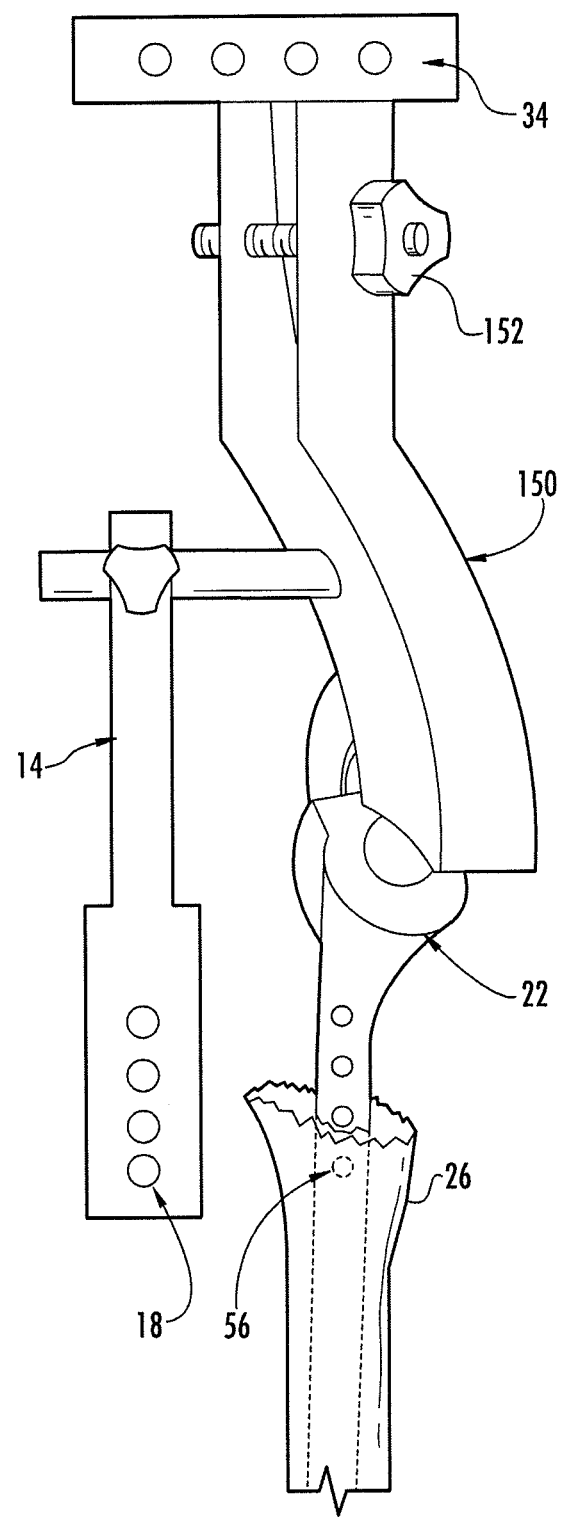
FIG. 20 is a perspective view of a broach assembly coupled to a jig assembly and a humeral implant that is positioned within the humeral shaft according to one embodiment of the present invention.
Figure 21:
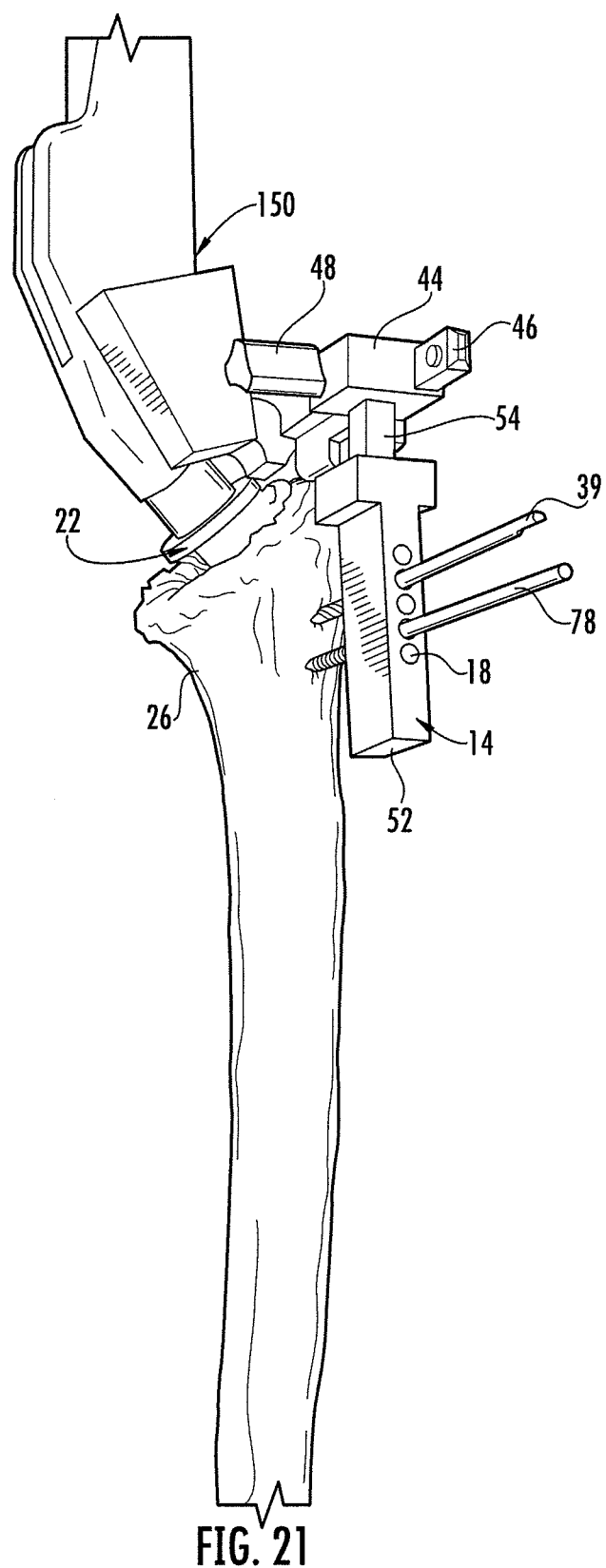
FIGS. 21 and 22 are perspective views of a broach assembly coupled to a jig assembly and a humeral implant that is positioned within the humeral shaft according to an embodiment of the present invention.
Figure 22:
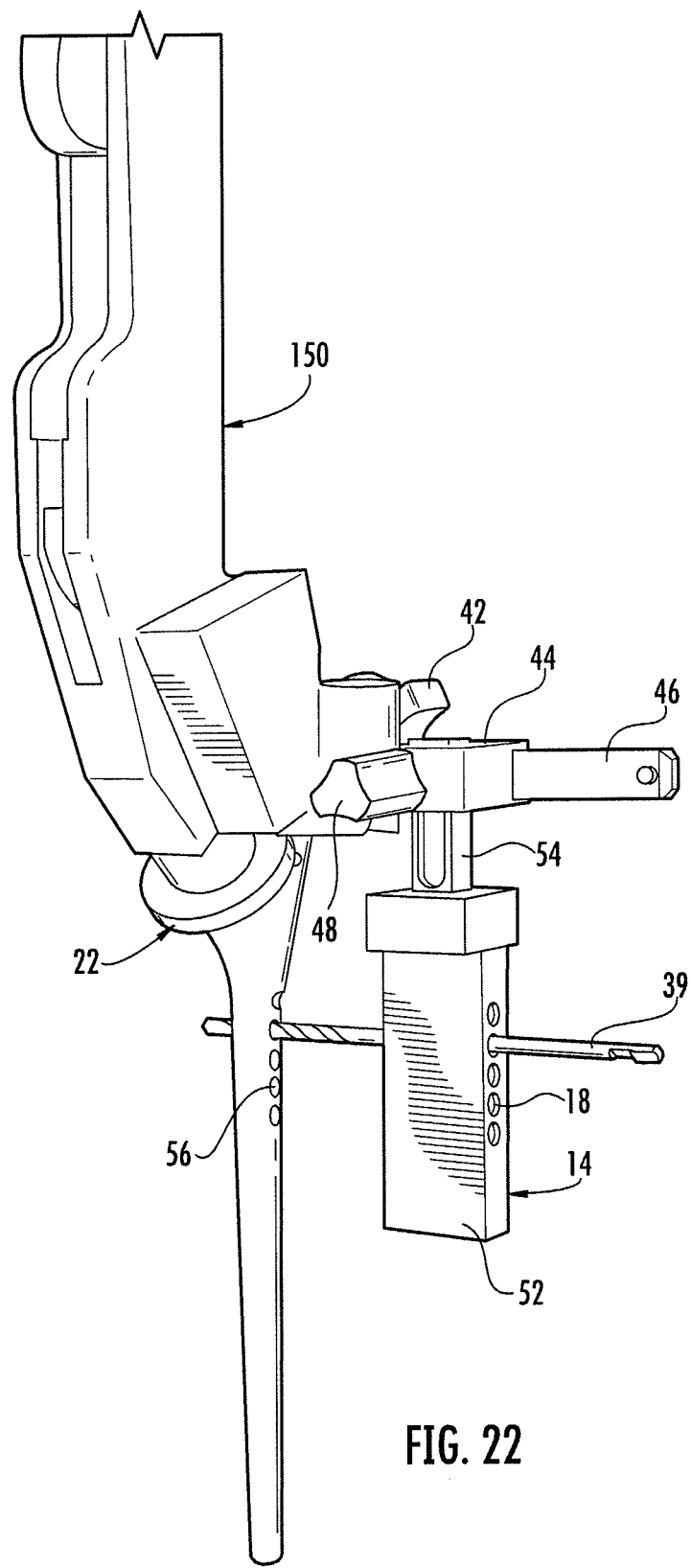
Figure 23:
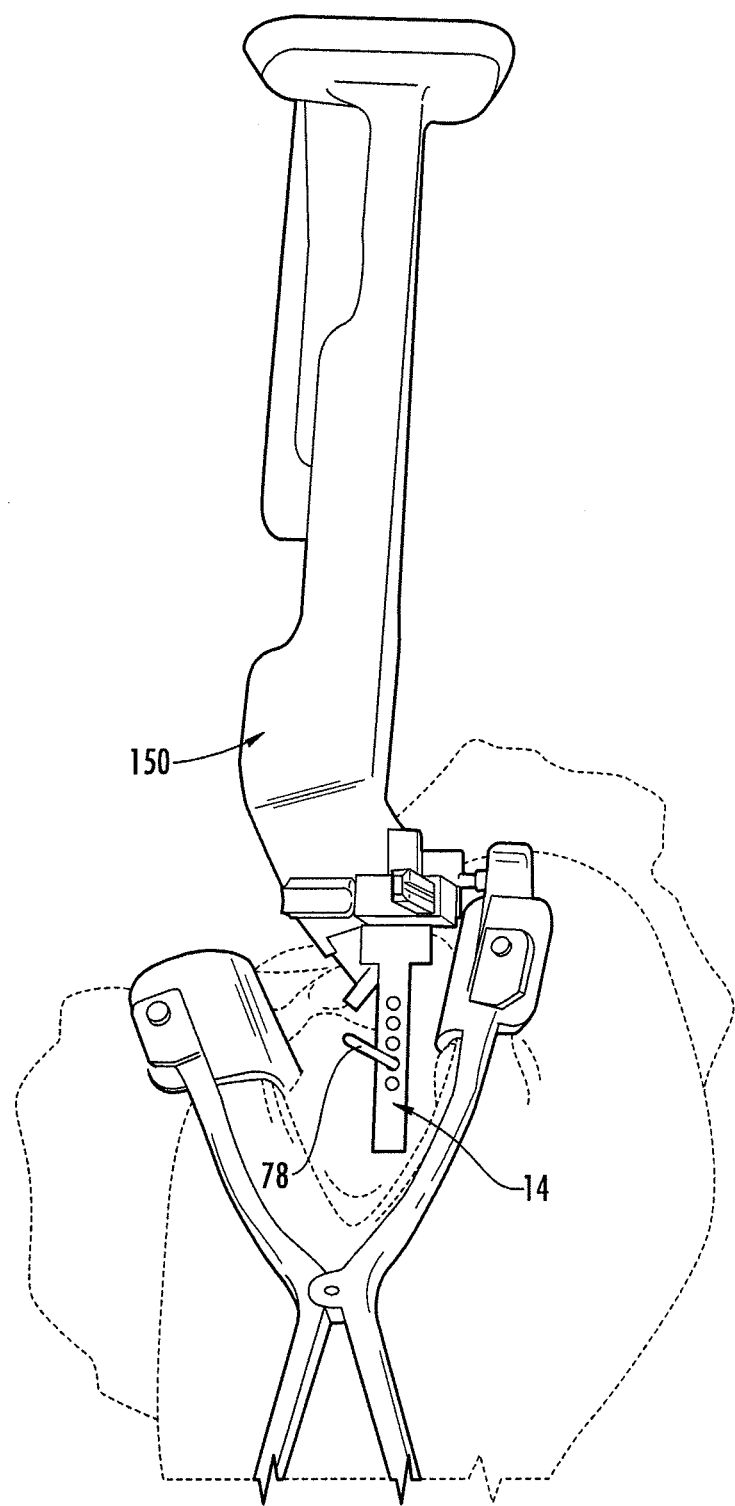
FIG. 23 is a photograph of a surgical procedure employing the broach assembly shown in FIGS. 21 and 22 and the jig assembly shown in FIG. 1 for positioning a humeral implant within the humeral shaft.

FIGS. 15-19 illustrate another embodiment of a humeral implant 80. Namely, the humeral implant 80 is modular and includes a stem 82, a body 84, and a head 86 that are sized and configured to be interchangeably coupled to one another. FIGS. 18 and 19 depict a trial humeral implant 80, and FIGS. 15-17 depict a final humeral implant. Each humeral implant 80 includes a stem 82 having a tapered opening 88 that is configured to receive a mating tapered end 90 of the body 84. The body 84 also includes a tapered opening 92 that is configured to receive a tapered post 94 of the head 86. The tapered end 90, post 94, and openings 88, 92 may be coupled, for example, with a standard or reverse Morse taper. FIGS. 16, 18, and 19 demonstrate that the body 84 may include a reverse Morse taper, while the tapered ends 90 and opening 88 may include a Morse taper. The humeral implant 80 may also include visible indicators (e.g., laser lines) for indicating the height 74 and rotational 96 location of the stem 82 within the humeral shaft.

Thus, the stem 82, body 84, and head 86 are engageable with one another and may be interchangeable. The tapered ends allow the stem 82, body 84, and head 86 to interlock with one another in a press fit. As such, a physician is able to implant the humeral implant 80 as a single interlocking piece or in a step-wise fashion. Moreover, because the stem 82, body 84, and head 86 are not permanently attached to one another, one or more of the components may be exchanged during or after implantation.

The humeral implant 80 may be various materials, such as a metal and/or polymer. For instance, the trial humeral implant 80 may include a metal stem 82 and a polymer body 84. In addition, the humeral implant 80 may be various sizes and configurations for accommodating different patients and injuries. For example, the body 84 may include three different stem/body sizes (e.g., 6/8 mm, 10/12 mm, or 14/16 mm stems and have a length that is small, medium, or long. Thus, the modular design may reduce the number of sizes of humeral implants needed given the flexibility in adjusting the position of the stem 82, body 84, and head 86. In addition, the humeral implant 80 may be sized and configured to be compatible with conventional heads 86.

According to another embodiment, a broach assembly 150 may be employed to guide one or more holes in the humeral shaft 26 for positioning a trial humeral implant 22 therein, as shown in FIGS. 20-23. The broach assembly 150 may be modified to include one or more holes 34 for determining the version of the humeral implant 22, as described above (see FIG. 20). In addition, the broach assembly 150 is configured to be coupled to the trial humeral implant 22 with a fastener 152 or other technique known to those of ordinary skill in the art. The jig assembly 14 may also be coupled to the broach assembly 150 with a fastener 42 in order to guide placement of a hole in one or more of the holes 56 in the trial humeral implant 22. For instance, a bicortical or unicortical hole may be formed directly through a hole 56 in the trial humeral implant 22 with a drill bit 39 that is guided by a hole 18 in the jig assembly 14 (see FIGS. 21 and 22). After a bicortical or unicortical hole has been formed in the humeral shaft 26, a cortical pin 78 may be inserted directly through the hole 56 in the trial humeral implant 22 and the hole formed in the humeral shaft, and a unicortical pin may be inserted in the humeral shaft. Thus, the broach assembly 150 may provide a step-saving technique whereby use of the longitudinal member 12 is unnecessary.

Figure 24:
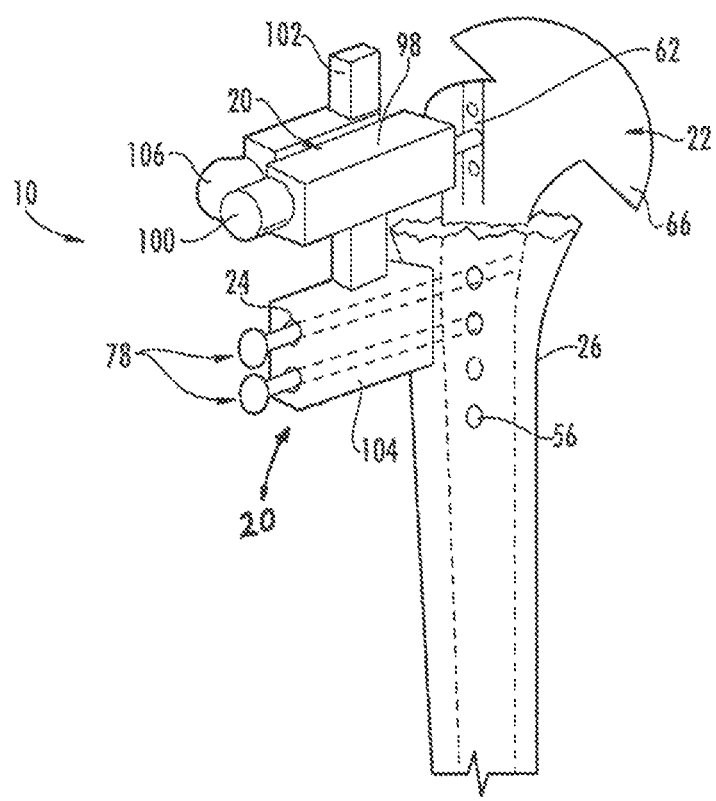
FIG. 24 is a perspective view of a fin clamp assembly secured to a humeral implant according to one embodiment of the present invention.
Figure 25:
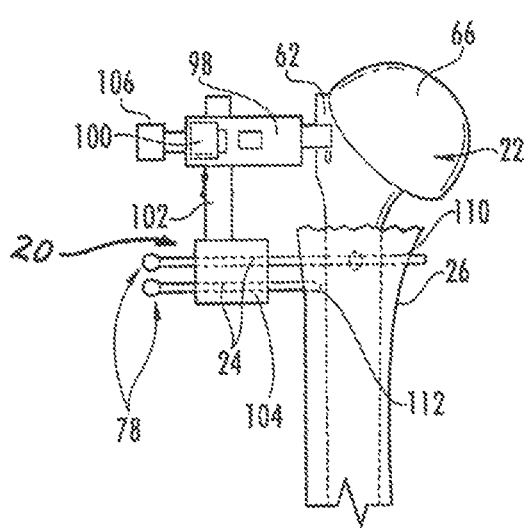
FIG. 25 is a side view of the fin clamp assembly and humeral implant shown in FIG. 24.
Figure 26:
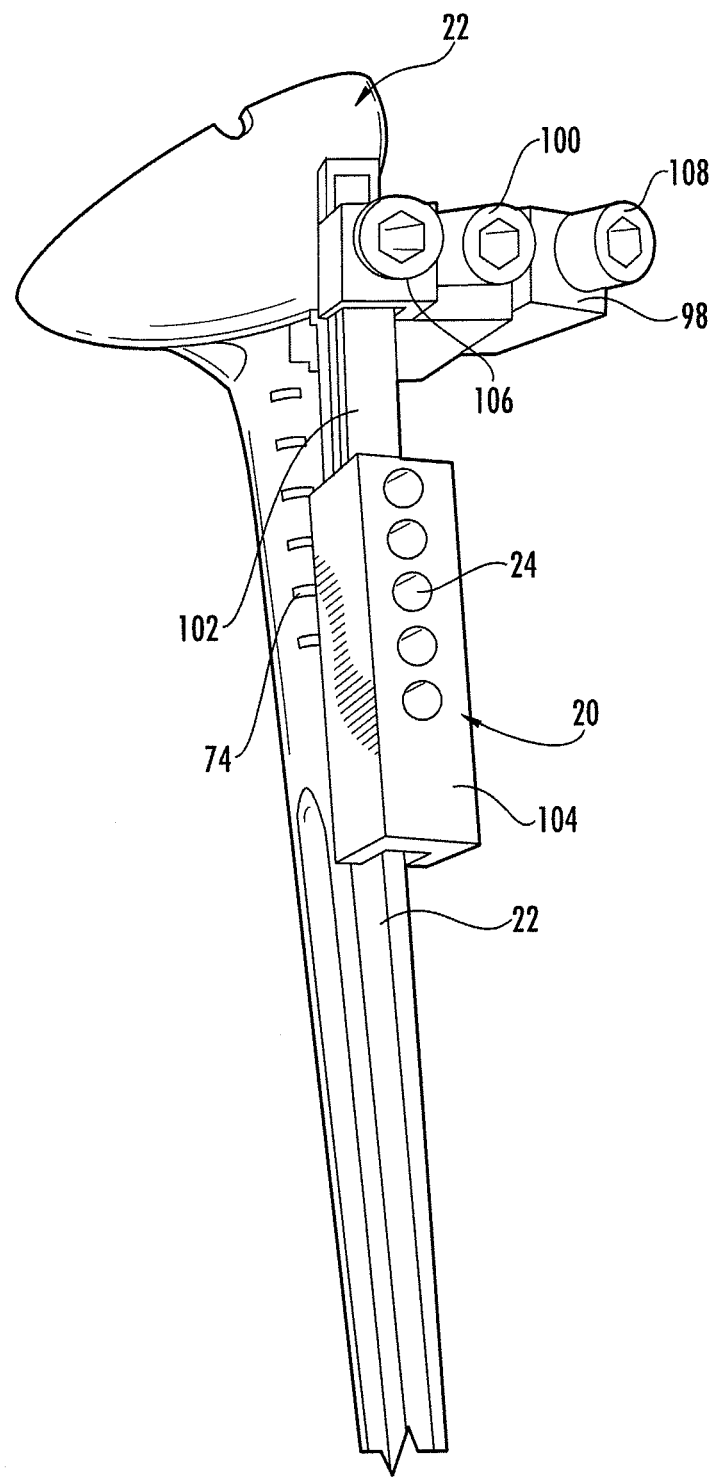
FIG. 26 is a front view of a fin clamp assembly coupled to a reverse shoulder humeral implant according to an embodiment of the present invention.
Figure 27:
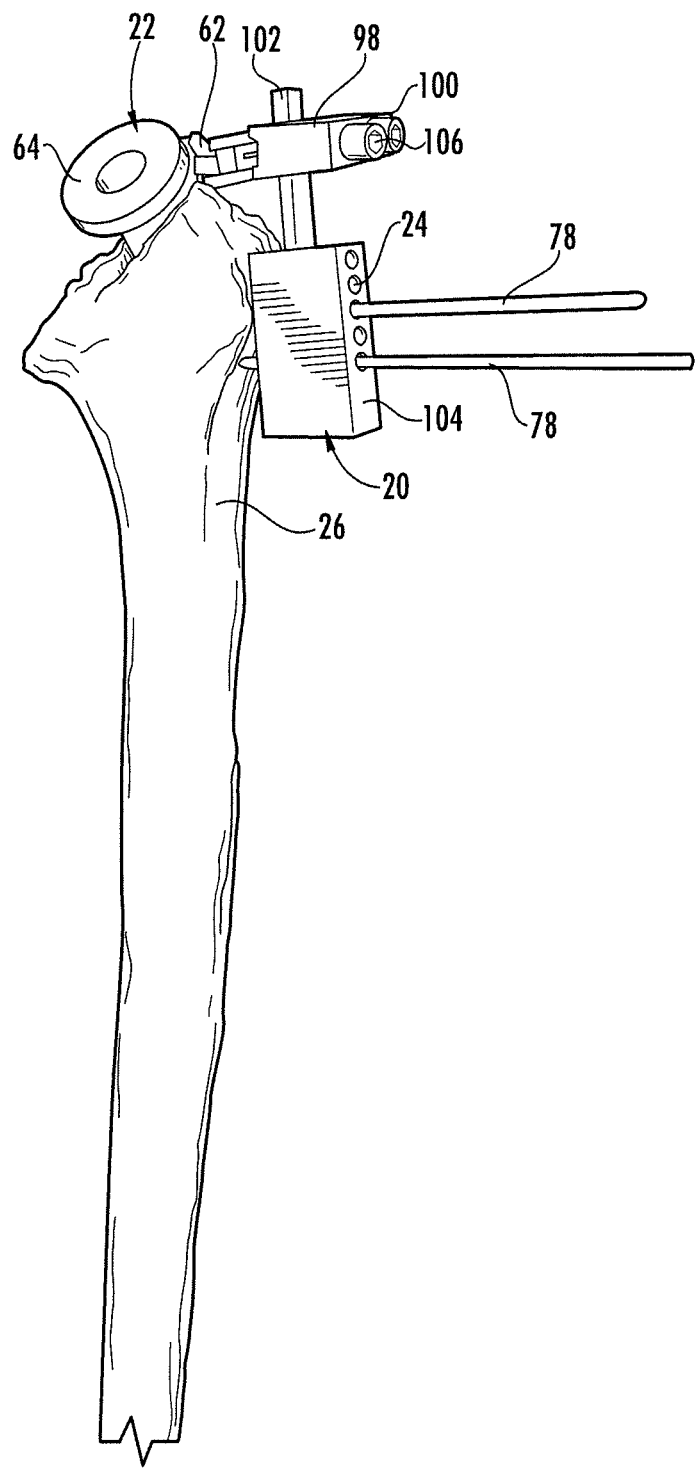
FIG. 27 is a perspective view of a humeral implant positioned within the humeral shaft and the fin clamp assembly shown in FIG. 26 coupled thereto.
Figure 28:
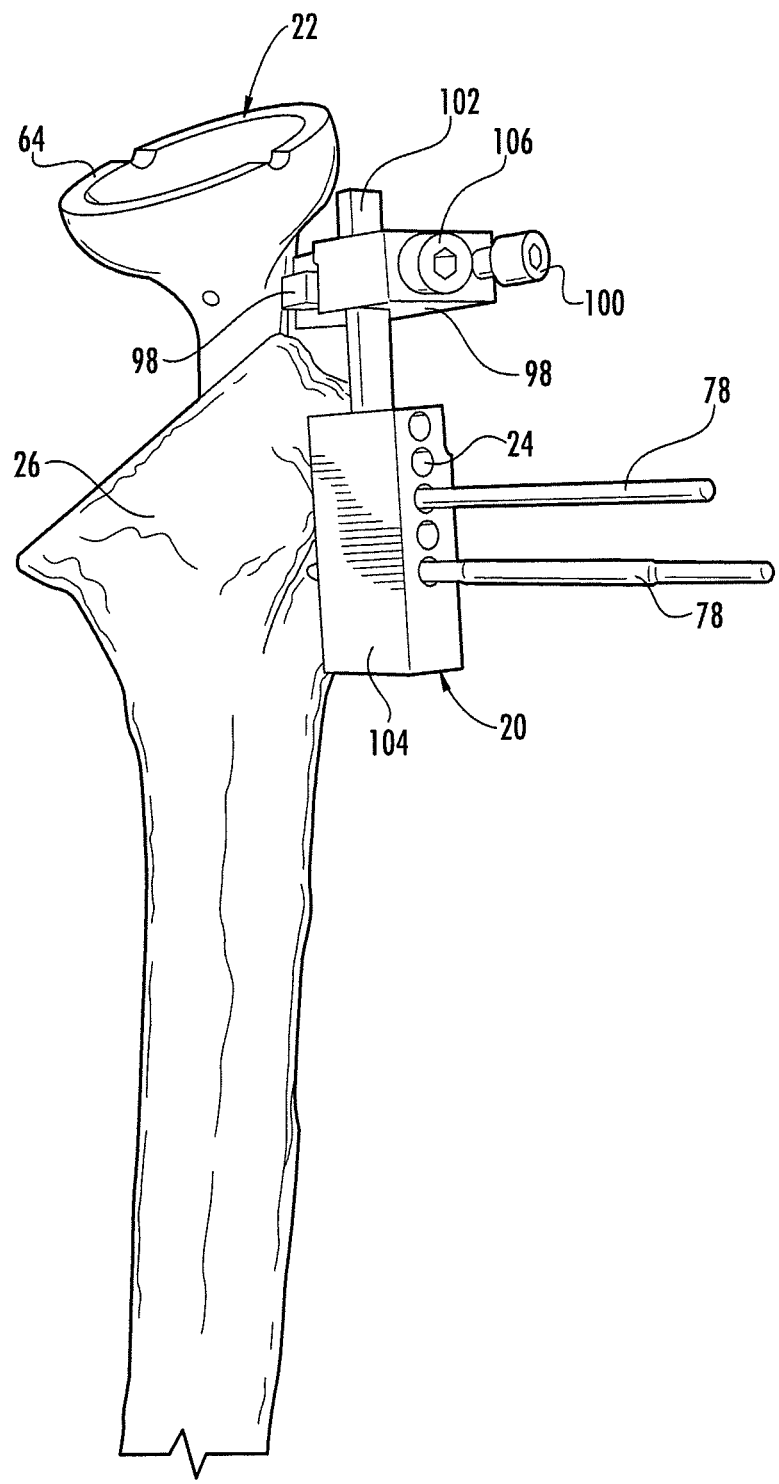
FIG. 28 is an enlarged perspective view of the reverse shoulder humeral implant and fin clamp assembly shown in FIG. 26.

FIGS. 24-28 illustrate a fin clamp assembly 20 according to one embodiment of the present invention. The fin clamp assembly 20 is employed to position the humeral implant 22 within the humeral shaft 26, as shown in FIGS. 24 and 25. The fin clamp assembly 20 includes a fin clamp 98 that is configured to be coupled to the humeral implant 22. In particular, the fin clamp 98 includes a first fastener 100 that is configured to secure the fin clamp to one of the fins 62 of the humeral implant 22. For instance, FIGS. 24 and 25 depict the fin clamp 98 secured to the anterior fin 62. The fin clamp 98 may be configured to engage one of the holes 70 or an indentation in the fin. The fin clamp assembly 20 also includes an extension member 102 and a pin guide 104. The fin clamp 98 includes an opening (not shown) that allows the pin guide 104 to be moved therethrough for adjusting the position thereof with respect to the fin clamp. A second fastener 106 may be employed to secure the fin clamp 98 to the extension member 102, thereby fixing the height of the pin guide 104. A third fastener 108 is shown and may also be used to secure the fin clamp 98 to the humeral implant 22, although typically only fasteners 100, 106 are necessary. A fin clamp 98 according to one embodiment of the present invention that may be employed with the fin clamp assembly 20 is disclosed by U.S. Pat. No. 6,277,123 to Maroney et al., which is incorporated herein by reference.

Furthermore, the fin clamp assembly 20 includes a plurality of holes 24 defined therethrough, wherein at least one of the holes is configured to align with a respective hole 56 in the humeral implant 22 and a hole formed in the humeral shaft 26. The holes 24 are each sized and configured to receive a pin 78 therethrough for locating the position of the humeral implant 22 and positioning the implant within the humeral shaft 26. For example, the holes 24 may be sized to receive a pin 78 having a diameter of about 3.2 mm. In one embodiment, the holes 24 are sized and configured such that the fin clamp assembly 20 is capable of being slid over the pins 78 while the pins are engaged in the humeral shaft 26. The pin guide 104 is shown as having two or five holes defined therein, however, it is understood that the pin guide may have one or more holes.

Figure 29:
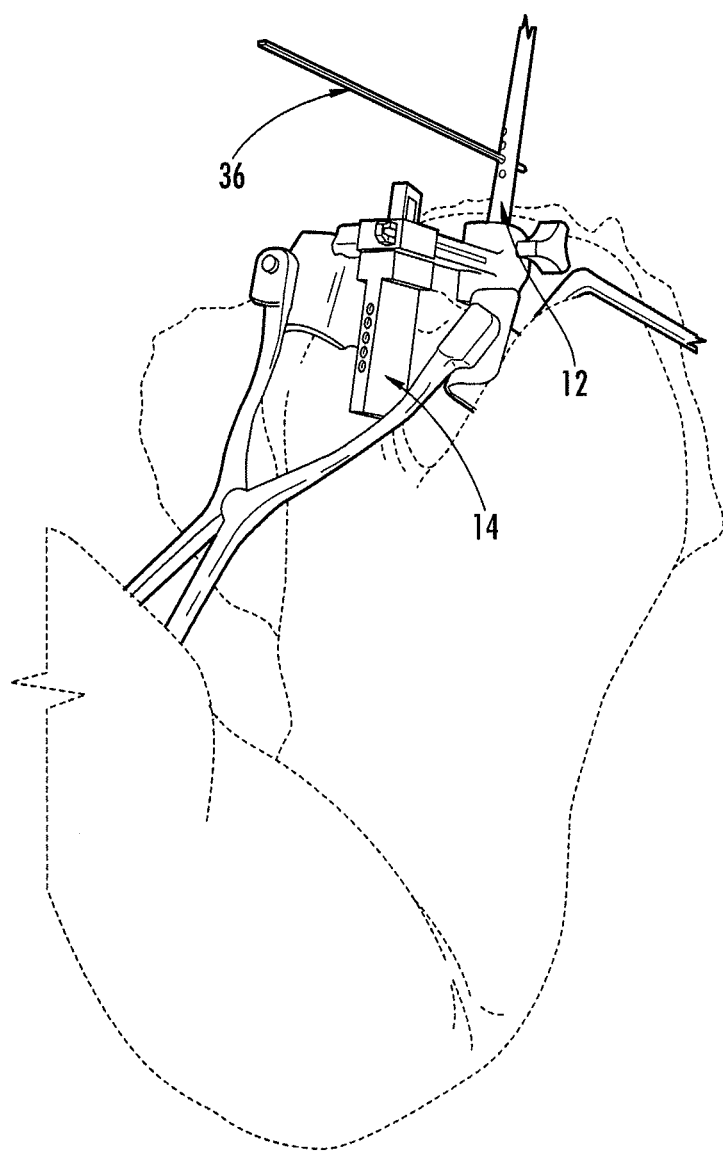
FIGS. 29-37 are photographs of a surgical procedure employing a system shown in FIG. 1 for treating a proximal humeral fracture.
Figure 30:
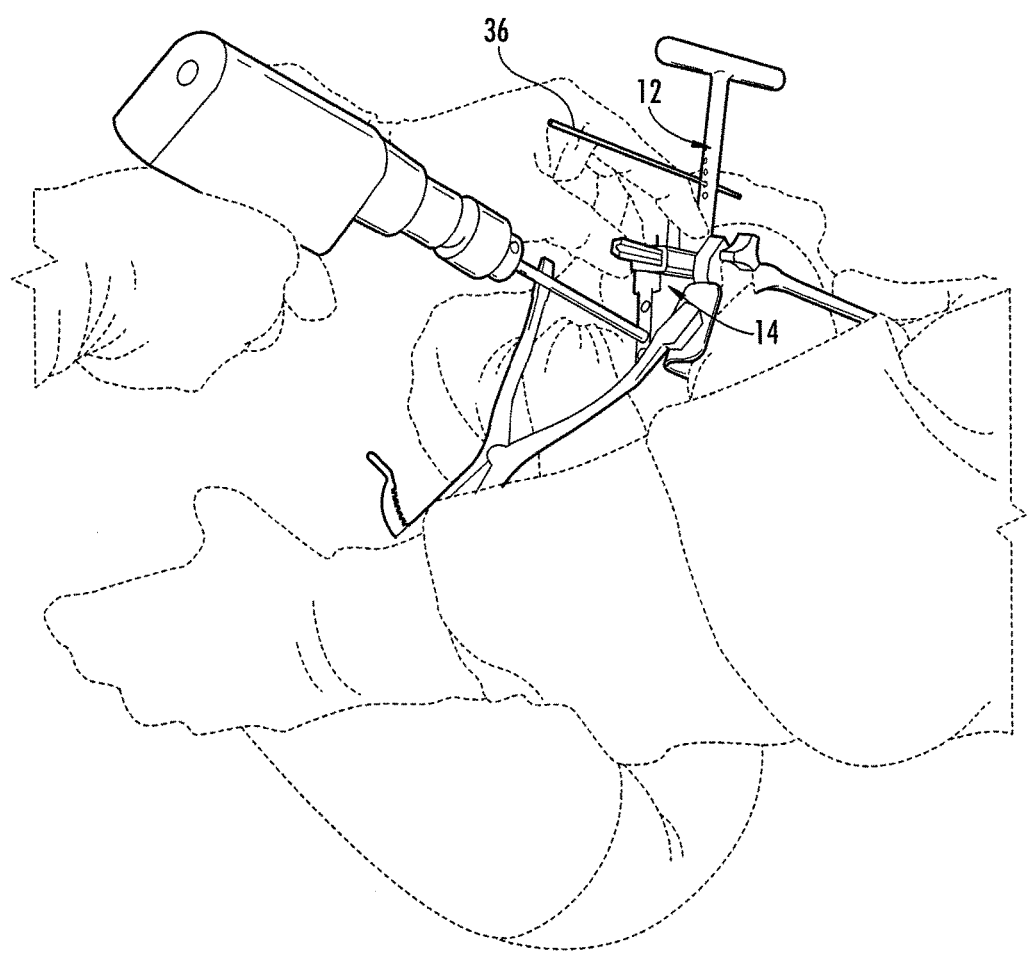

In use according to one embodiment of the present invention, the longitudinal member 12 is positioned within the reamed medullary canal of the humeral shaft 26 such that the coupling member 38 is positioned proximate to, or abuts, the proximal end of the fractured end of the humeral shaft 26. The jig assembly 14 is then coupled to the longitudinal member 12 with the fastener 42, and the position of the jig assembly is fixed with respect to the longitudinal member with fastener 48. Typically, the longitudinal member 12 and jig assembly 14 are coupled prior to inserting the longitudinal member within the humeral shaft 26, although the longitudinal member could be positioned within the humeral shaft before attaching the jig assembly thereto. In order to determine the version of the humeral implant 22, an orientation pin 36 may be inserted through one of the holes 34 defined in the longitudinal member 12. According to one embodiment, the orientation pin 36 is inserted within a hole 34 located between 0 and 40 degrees of version such that the pin aligns with the longitudinal axis of the patient's forearm (see FIG. 29). Once the physician is satisfied with the version and the position of the longitudinal member 12 and jig assembly 14, the physician will get an idea of the size of the humeral implant 22 that will be necessary. Depending on the size of the humeral implant 22 needed, the physician will insert a drill bit 39 through one of the holes 18 in the jig assembly 14 and into a corresponding aligned hole 16 in the longitudinal member 12 and form a first hole 110 in the humeral shaft 26 (see FIGS. 9 and 30). The physician may then drill a second hole 112 in the humeral shaft 26 with the drill bit 39 that is guided through a second hole 18. The first hole 110 may be a bicortical or unicortical hole formed in the humeral shaft 26, while the second hole 112 may be a unicortical hole formed inferior to the first bicortical or unicortical hole 110 (see FIG. 25). The second unicortical hole 112 may be placed through one of the openings 18, 24 in the jig assembly 14 or fin clamp assembly 20, respectively. Alternatively, a threaded unicortical pin can be utilized in place of drilling the second hole 112. Another alternative would be to eliminate the use of the unicortical hole 112 and associated pin and, instead, utilize the first hole 110 as the only fixation point.

Figure 31:
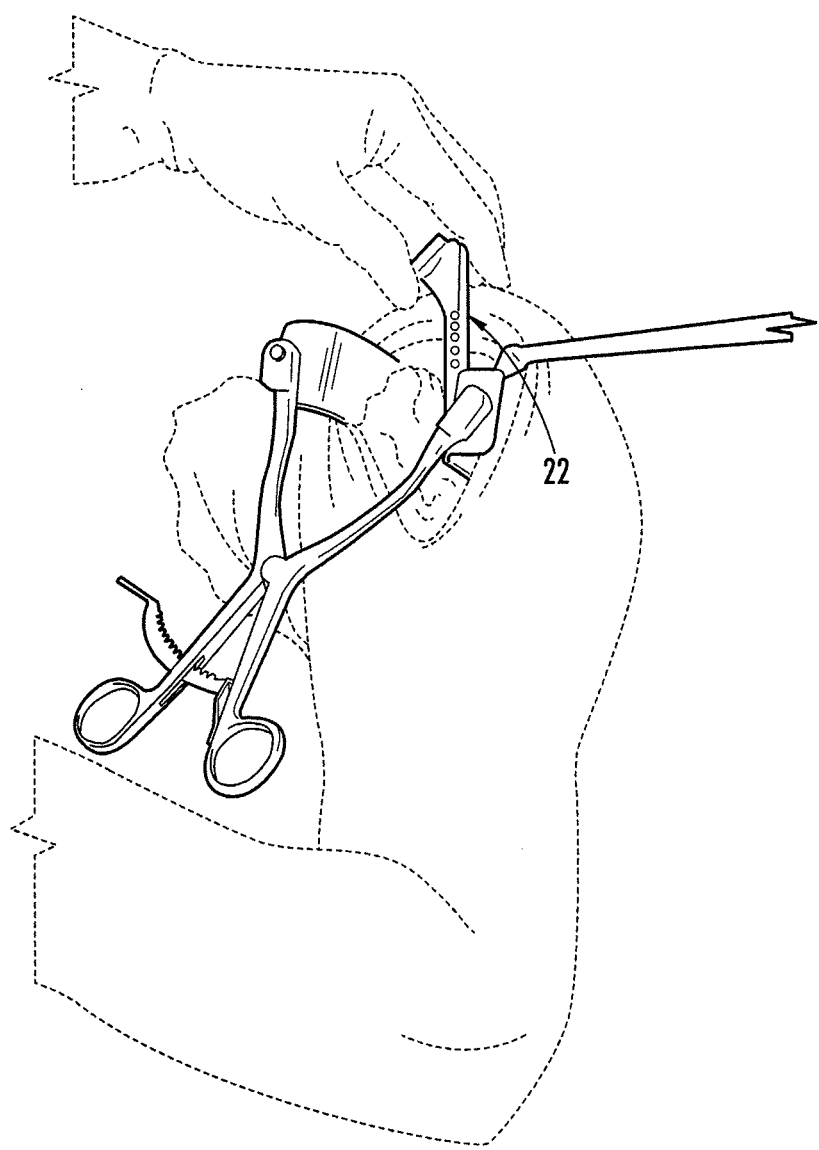
Figure 32:
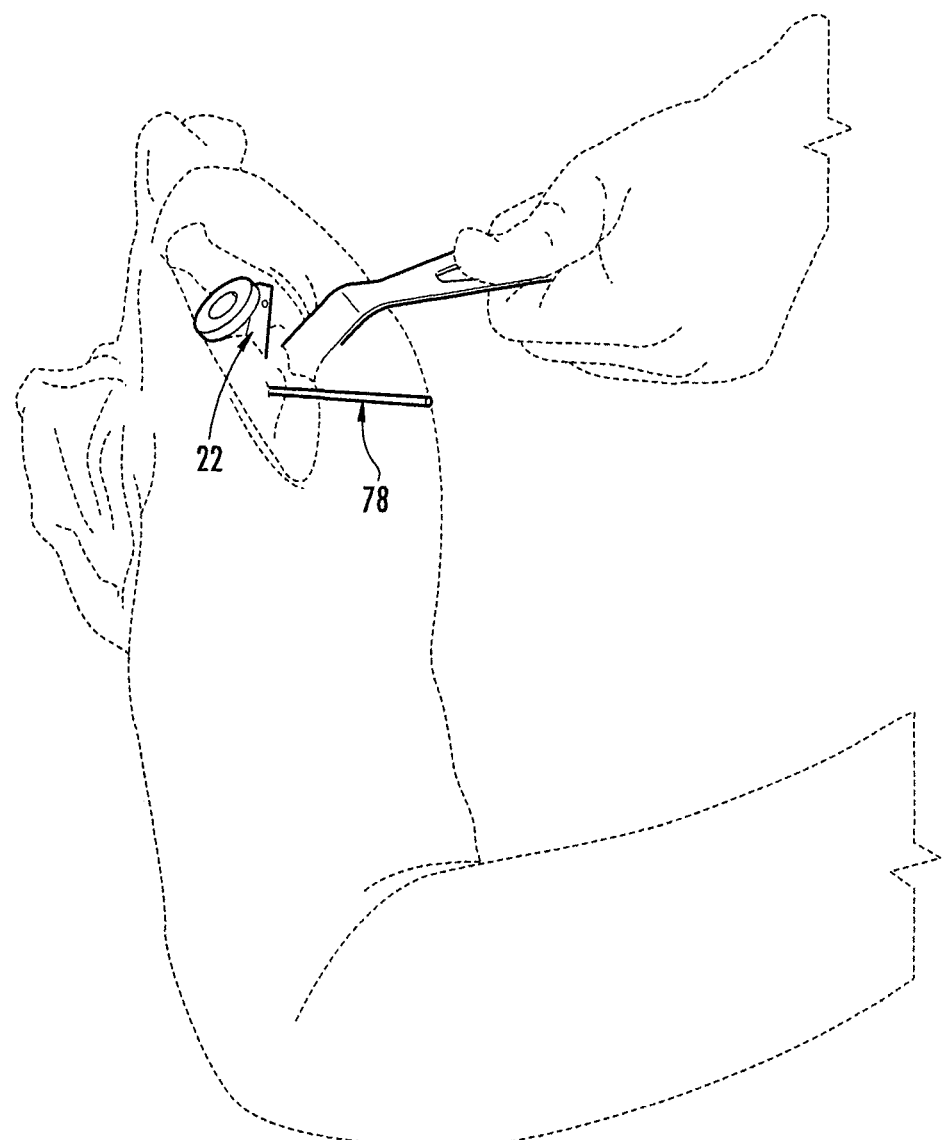
Figure 33:
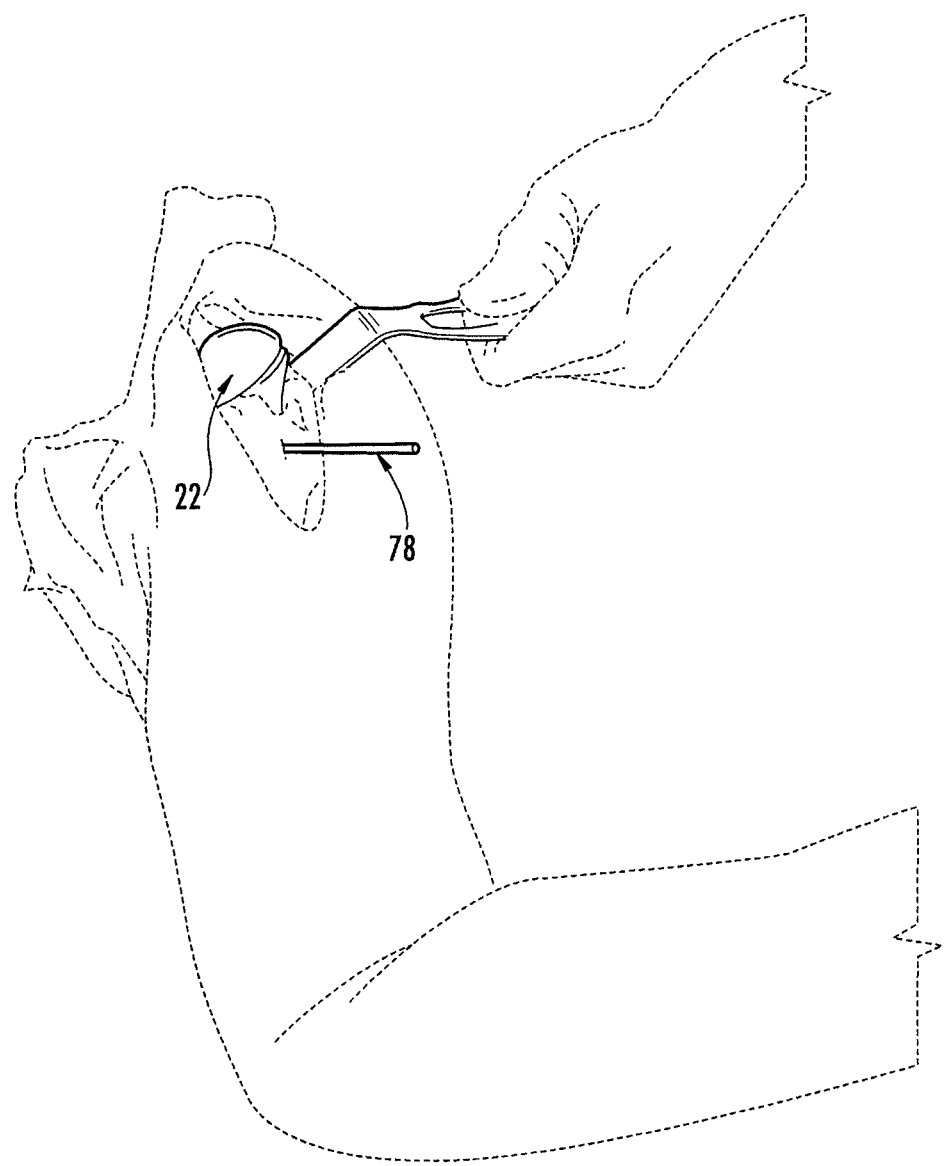
Figure 34:
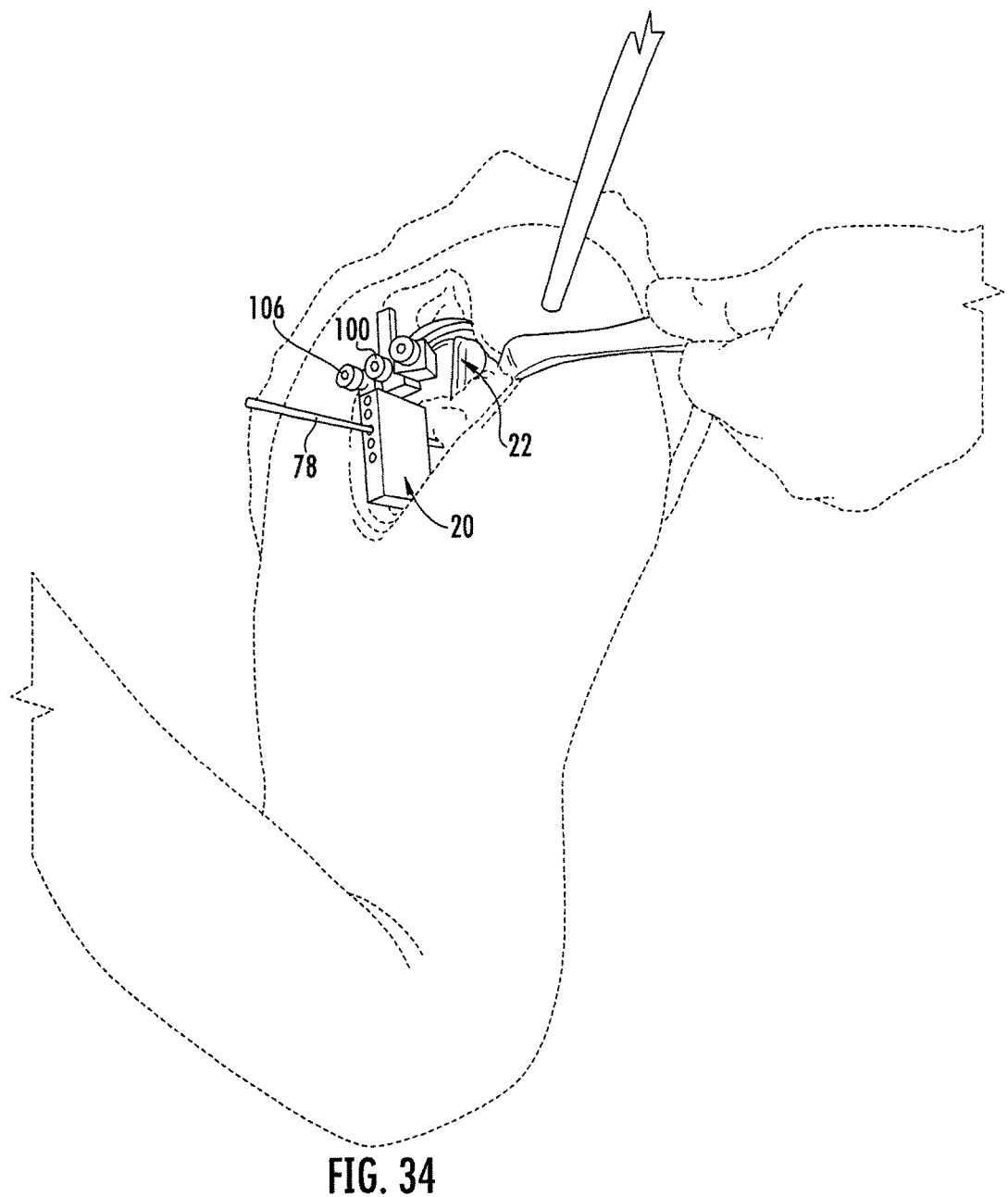
Figure 35:
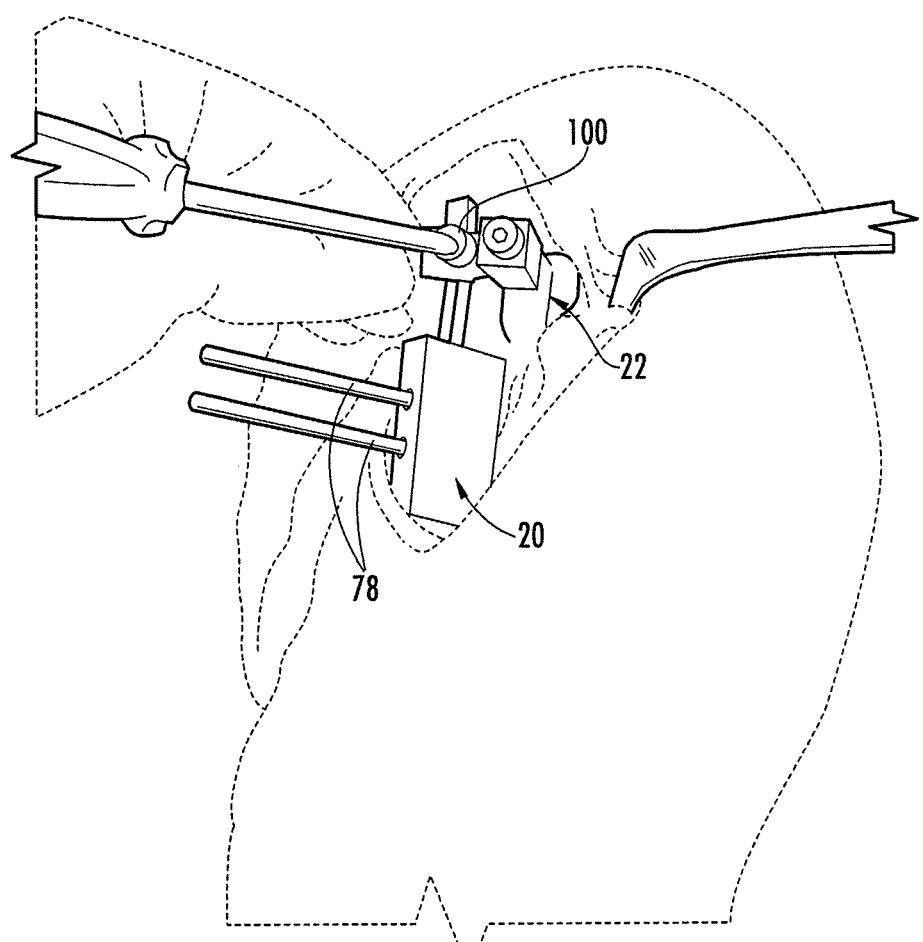
Figure 36:
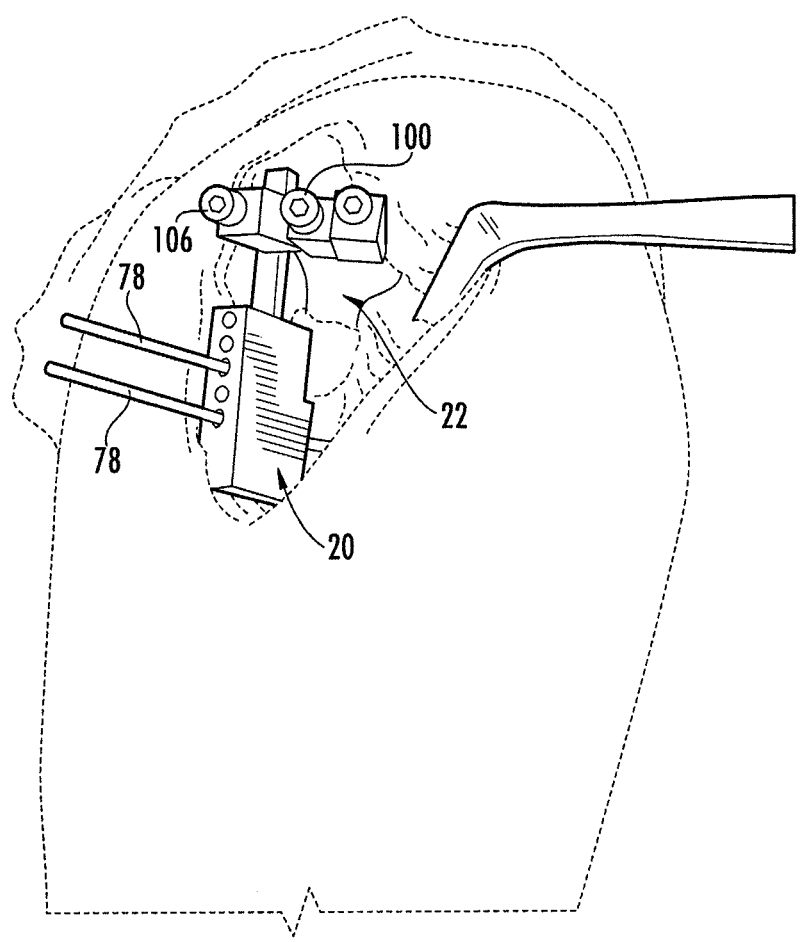
Figure 37:
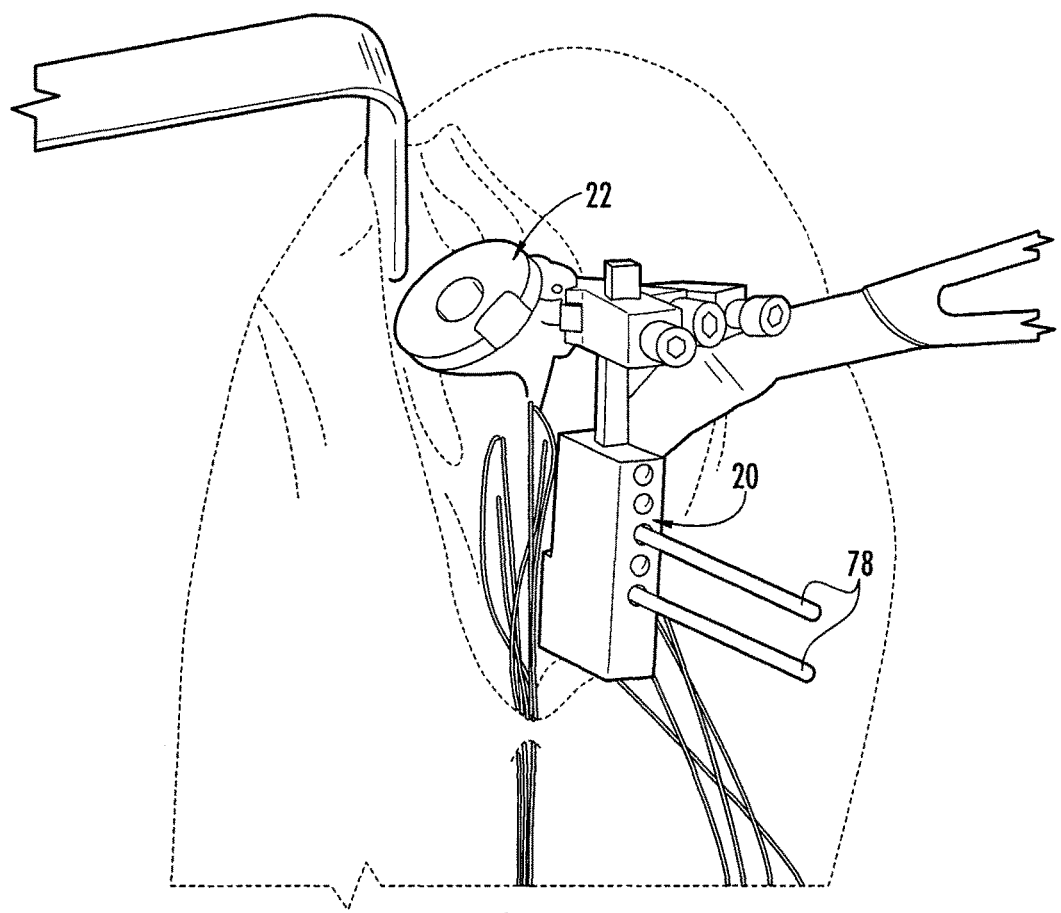

Once the holes have been formed in the humeral shaft 26, the longitudinal member 12, jig assembly 14, and orientation pin 26 may be removed from the humeral shaft. A trial humeral implant 22 may then be inserted within the medullary canal of the humeral shaft 26 (see FIG. 31). At this time the physician may then adjust the height of the trial implant 22 by choosing the appropriate hole 56 in the trial humeral implant 22. The physician then inserts a pin 78 through the first hole 110 and into the humeral shaft 26 and through one of the holes 56 defined in the trial humeral implant 22 (see FIGS. 24, 25, 27, 28, 32, and 33). The physician may then also insert a second pin 78 into the second hole 112, but the hole is unicortical such that the pin does not engage the trial humeral implant (see FIGS. 25 and 35-37). Next, the physician may slide the fin clamp assembly 20 over the pins 78, adjust the height of the pin guide 104 if necessary using the extension member 102 and fastener 106, and secure the fin clamp 98 to the anterior fin 62 of the trial humeral implant 22 using the fastener 100 (see FIGS. 34-37). The physician can note the height of the trial humeral implant 22 based on experience and/or the height indicators 74.

Once the position of the fin clamp assembly 20 and humeral implant 22 have been determined, the fin clamp may be removed from the trial humeral implant 22. The cortical pin 78 is retracted from the trial humeral implant 22, and the trial humeral implant is removed from the humeral shaft 26. Bone cement is mixed and provided in the medullary canal in preparation for receiving the final humeral implant 22. The final humeral implant 22 is inserted in the medullary canal, and the fin clamp assembly 20 is again slid over the pins 78. The fin clamp 98 is then secured to the anterior fin 62 in the same position that was noted when determining the location of the trial humeral implant 22. The fin clamp assembly 20 is left in position until the bone cement cures, and then the fin clamp assembly and pins 78 are removed. The drill holes 110, 112 for the pins 78 are proximal in the remaining humeral shaft 26 and can be filled with a small amount of bone graft to prevent any cement extrusion, if desired. Or, the physician may insert a fastener (not shown) through one or both of the holes 110, 112 to further fixate the humeral implant 22 within the humeral shaft 26.

Therefore, embodiments of the present invention may provide several advantages. For example, the system 10 may provide techniques for accurately locating a humeral implant 22 within a fractured humeral shaft 26 for both shoulder hemiarthroplasty and reverse arthroplasty. The system 10 may also accurately determine both version and height for the humeral implant 22. For reverse arthroplasty, the system is robust by utilizing cortical fixation of the pin 78 through the trial humeral implant 22. This fixation may accommodate the forces necessary to assess tensioning and joint stability. The system 10 is less bulky than conventional systems and offers a simpler technique to slave the final trial position to the final implant position. Furthermore, for hemiarthroplasty, surgical dissection is minimized, and the ease of changing height intraoperatively is greatly enhanced. In both reverse arthroplasty and hemiarthroplasty, the system 10 may be built around current surgical instrumentation, which reduces the need to significantly redesign current surgical instruments and techniques.

Many modifications and other various embodiments of the invention set forth herein will come to mind to one skilled in the art to which this invention pertains having the benefit of the teachings presented in the foregoing descriptions and the associated drawings. Therefore, it is to be understood that the various embodiments of the invention are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for treating a proximal humeral shaft fracture with a humeral implant having at least one hole defined therethrough, the method comprising:
    inserting at least a distal portion of a longitudinal rod member within the humeral shaft, wherein the distal portion of the longitudinal rod member includes a plurality of holes extending therethrough and spaced axially apart from one another;
    coupling a jig assembly comprising at least one hole extending therethrough to a coupling member included on the longitudinal rod member, wherein the coupling member is disposed on the longitudinal rod member between the at least distal portion and a proximal portion of the longitudinal rod member and configured to abut against a proximal end of the humeral shaft, wherein the at least one hole of the jig assembly is configured to align with at least one of the plurality of holes of the distal portion of the longitudinal rod member;
    wherein the proximal portion of the longitudinal rod member comprises a plurality of holes that are offset radially and axially along the longitudinal member from one another, wherein the method further comprises inserting an orientation pin in one of the first plurality of holes to determine the version of the humeral implant in the humeral shaft;
    wherein the jig assembly comprises a coupling member configured to mate with the coupling member of the longitudinal rod member for removably securing the jig assembly to the longitudinal rod member between the proximal and distal portions of the longitudinal rod member without overlap of the plurality of holes of the proximal portion of the longitudinal rod member, the jig assembly comprises an arm extending from the coupling member of the jig assembly and alongside of the humeral shaft, and wherein the at least one hole extends through the arm in a perpendicular direction to the direction of the arm;
    forming at least one hole in the humeral shaft guided by the at least one hole of the jig assembly and the at least one of the plurality of holes of the distal portion of the longitudinal rod member; and
    after forming the at least one hole in the humeral shaft, removing the longitudinal rod member from the humeral shaft and inserting at least a distal portion of the humeral implant within the humeral shaft, wherein the at least one hole formed in the humeral shaft is configured to align with at least one hole extending through the humeral implant such that the jig assembly is configured to locate the position of the humeral implant in the humeral shaft.

2. The method of claim 1, wherein the humeral implant is a trial humeral implant, the method further comprising inserting the trial humeral implant within the humeral shaft, and inserting a cortical pin through the at least one hole in the humeral shaft and the at least one hole defined the trial humeral implant.

3. The method of claim 2, further comprising sliding a fin clamp assembly over the cortical pin and fastening the fin clamp to the trial humeral implant.

4. The method of claim 3, further comprising unfastening the fin clamp and removing the cortical pin and the trial humeral implant, inserting a final humeral implant within the humeral shaft, inserting the cortical pin through the at least one hole in the humeral shaft and at least one hole defined the final humeral implant, and sliding the fin clamp assembly over the cortical pin such that the fin clamp is fastened to the final humeral implant in the same way as the fin clamp was fastened to the trial humeral implant.

* * * * *